(12) United States Patent  (10) Patent No.: US 8,263,128 B2
Curatolo et al.  (45) Date of Patent: Sep. 11, 2012

(54) SOLID PHARMACEUTICAL DISPERSIONS WITH ENHANCED BIOAVAILABILITY

(75) Inventors: William J. Curatolo, Niantic, CT (US); Scott M. Herbig, East Lyme, CT (US); James A. S. Nightingale, Bend, OR (US)

(73) Assignee: Bend Research, Inc., Bend, OR (US)

( * ) Notice: Subject to any disclaimer, the term of this patent is extended or adjusted under 35 U.S.C. 154(b) by 279 days.

(21) Appl. No.: 09/770,562

(22) Filed: Jan. 26, 2001

(65) Prior Publication Data

US 2002/0009494 A1   Jan. 24, 2002

Related U.S. Application Data

(63) Continuation of application No. 09/131,019, filed on Aug. 7, 1998, now abandoned.

(60) Provisional application No. 60/055,221, filed on Aug. 11, 1997.

(51) Int. Cl.
*A61K 9/14* (2006.01)
*A61K 9/16* (2006.01)
*A61K 31/40* (2006.01)
*A61K 31/44* (2006.01)

(52) U.S. Cl. ......... 424/489; 424/497; 514/419; 514/345

(58) Field of Classification Search .................. 424/489, 424/499, 497; 514/419, 345, 595
See application file for complete search history.

(56) References Cited

U.S. PATENT DOCUMENTS

| | | | |
|---|---|---|---|
| 4,127,647 A | 11/1978 | Sato et al. | 424/78 |
| 4,831,031 A | 5/1989 | Lowe, III et al. | 514/254 |
| 4,983,593 A * | 1/1991 | Miyajima et al. | 514/110 |
| 5,013,557 A | 5/1991 | Tai | |
| 5,456,923 A * | 10/1995 | Nakamichi et al. | 424/489 |
| 5,576,025 A * | 11/1996 | Akiyama et al. | 424/501 |
| 5,700,485 A | 12/1997 | Berde et al. | 424/501 |
| 5,723,269 A | 3/1998 | Akagio et al. | 424/497 |
| 5,858,411 A | 1/1999 | Nakagami et al. | 424/489 |
| 6,147,072 A * | 11/2000 | Bymaster et al. | 514/220 |
| 6,165,506 A | 12/2000 | Jain et al. | |
| RE37,053 E | 2/2001 | Hanes et al. | |
| 6,254,889 B1 | 7/2001 | Kigoshi et al. | 424/487 |
| 6,303,148 B1 | 10/2001 | Hennink et al. | |
| 6,395,302 B1 | 5/2002 | Hennink et al. | |
| 6,497,903 B1 | 12/2002 | Hennink et al. | |
| 6,610,317 B2 | 8/2003 | Straub et al. | |
| 6,800,297 B2 | 10/2004 | Altreuter et al. | |
| 7,060,296 B2 | 6/2006 | Hennink et al. | |
| 7,078,057 B2 | 7/2006 | Kerkhof | |

(Continued)

FOREIGN PATENT DOCUMENTS

EP   0 344 603   * 12/1989

(Continued)

OTHER PUBLICATIONS

Yamaguchi et al., Yakuzaigaku 53(4): 221-228, 1993.*

(Continued)

*Primary Examiner* — Blessing Fubara

(74) *Attorney, Agent, or Firm* — Klarquist Sparkman, LLP

(57) ABSTRACT

Spray dried solid dispersions comprising a sparingly soluble drug and hydroxypropylmethylcellulose acetate succinate (HPMCAS) provide increased aqueous solubility and/or bioavailability in a use environment.

23 Claims, 1 Drawing Sheet

U.S. PATENT DOCUMENTS

| | | | |
|---|---|---|---|
| 7,300,919 | B2 | 11/2007 | Patton |
| 7,404,828 | B1 | 7/2008 | Nicola |
| 7,521,069 | B2 | 4/2009 | Patton et al. |
| 2006/0210640 | A1 | 9/2006 | Kerkhof |

FOREIGN PATENT DOCUMENTS

| | | | |
|---|---|---|---|
| EP | 0344603 | | 12/1989 |
| EP | 0380219 | | 8/1990 |
| EP | 0413299 | | 2/1991 |
| EP | 0421581 | | 4/1991 |
| EP | 0421582 | | 4/1991 |
| EP | 0 784 974 | * | 7/1997 |
| EP | 0784974 | | 7/1997 |
| EP | 0852140 | | 7/1998 |
| EP | 1027885 | | 8/2000 |
| EP | 0852140 | | 12/2003 |
| EP | 1741424 | | 1/2007 |
| EP | 0901786 | | 6/2007 |
| GB | 2132495 | | 7/1984 |
| JP | 57-176907 | * | 10/1982 |
| JP | 57176907 | | 10/1982 |
| JP | 61227524 | | 9/1986 |
| JP | 2-15027 | * | 1/1990 |
| JP | 0215027 | | 1/1990 |
| JP | 7126153 | | 5/1995 |
| WO | WO9619239 | | 6/1996 |
| WO | WO9635414 | | 11/1996 |
| WO | WO9706781 | | 2/1997 |
| WO | WO9710811 | | 3/1997 |
| WO | WO9734610 | | 9/1997 |
| WO | WO00/13672 | | 3/2000 |
| WO | WO01/45674 | | 6/2001 |
| WO | WO01/45677 | | 6/2001 |

OTHER PUBLICATIONS

Obara et al. ("Influence of processing variables on the properties of free films prepared from aqueous polymeric dispersions by a spray technique," in International Journal of Pharmaceutics 126 (1995) 1-10).*

Abstract of Madhusoodanan et al. ("Efficacy of risperidone treatment for psychoses associated with schizophrenia, schizoaffective disorder, bipolar disorder, or senile dementia in 11 geriatric patients: a case series," in J Clin Psychiatry. Nov. 1995;56(11):514-8 (Abstract enclosed).*

Toshio Yamaguchi et al., 1993, vol. 53, No. 4, pp. 221-228 (XP002121600) English Version.

Takeuchi et al., 35 Chem. Pharm. Bull. 3800-3806, 1987.

Dangprasirt et al., 21 Drug development and Industrial Pharmacy, 2323-2337, 1995.

Takeichi et al., Chem. Pharm. Bull, 38(9), 2547-2551, 1990.

Baba, et al., Chem. Pharm. Bull, 38(9), 2542-2546, 1990.

T. Yamaguchi et al. Yakuzaigaku, 53(4), 221-228, 1993.

Toshiya Kai, et al., 1996, Pharmaceutical Society of Japan, pp. 568-571.

Lucy S. C. Wan, et al., Drug Development and Industrial Pharmacy, 18(9), 997-1001, 1992.

Perry's Chemical Engineers' Handbook Sixth Edition, Robert H. Perry, et al., 1984, 20-54 / 20-57.

T. Yamaguchi et al. Yakuzaigaku, 53(4), 221-228, 1993 (English Version).

Noriaki Ohnishi, et al., Chem.. Pharm. Bull., 35(9), pp. 3935-3939, 1987.

Alan K. Hilton et al., Jrnl of Pharmaceutical Sciences, vol. 82, No. 7, pp. 737-743, 1993.

Opposition Statement for Opponent IV.

Toshio Yamaguchi et al., Yakuzaigaku, vol. 53, No. 4, pp. 221-228, 1993 (English Translation).

Notice of Opposition and Opposition Statement for Opponent III.

Yamaguchi T. et al., Yakuzaigaku, 53(4), pp. 221-228, 1993.

Translation of JP-A-57-176907.

Takeuchi H. et al., Chem. Pharm. Bull, 35(9), pp. 3800-3806, 1987.

Kai et al., Chem. Pharm. Bull. 44(3), pp. 568-571, 1996.

Notice of Opposition from Opponent 2.

D2a—translation of Yamaguchi et al., Yakuzaigaku 53(4), pp. 221-228, 1993.

D4—Gennaro A. R., in Remington: The Science and Practice of Pharmacy, $20^{th}$ Ed., 2000, pp. 681-682.

D5—EP98305960.1, Mar. 17, 1999, as originally filed.

D7—Excerpt of the file history of EP 98305960.1.

D9—Laid open Japanese patent application S61-227524, Oct. 9, 1986.

D9a—translation of laid open Japanese patent application S61-227524 into English, Oct. 9, 1986.

D10a—Translation of WO 96/19239, Jun. 27, 1996.

D14—E-mail exchange between Dr. Frank Daelemans of Johnson & Johnson, Prof. Yamamoto and Dr. Yamaguchi btwn Oct. 29, 2007 and Nov. 5, 2007.

D15—Declaration by Prof. Masaharu Miyajima co-inventor of D3, Jan. 31, 2008.

D16—Spray Drying Handbook, K. Masters Longman Scientific & Technical, 1991.

D17—Definition of solubility from US Pharmacopeia USP23, Jan. 1, 1995.

D18—Declaration of Dr. Shen Yun Luk, Mar. 12, 2008 (with appendix A, B and C).

Notice of Opposition and Opponent 1 Opposition Statement.

Brief Communication—letter from Opponent I with confirmation OI Opposition Statement.

A1—Yamaguchi et al., Yakuzaigaku, 53(4), 221-228, 1993.

A2—English language translation of Yamaguchi et al., Yakuzaigaku, 53(4).

A14—Patentee's letter of May 19, 2003.

A15—Patentee's letter of Aug. 28, 2006.

A16—Exhibit A (Submitted by Patentee on Oct. 19, 2006).

A21—Perry's Chemical Engineers' Handbook, Sixth Edition (R. H. Perry, D, W. Green, J. O. Maloney, eds) McGraw-Hill Book Co. 1984, p. 20-54 to 20-57.

A22—Declaration of Dr Shin Itakura.

A23—Spray Drying Handbook Fifth Edition, (K Masters), 1991, pp. 1 to 4.

A24—Spray Drying—Maturity or Opportunities?, (Richard E. Bahu), in Drying '92, ed. A S Mujumdar, 1992, pp. 74-76.

A25—Spray Drying and Supercritical Fluid Particle Generation Techniques (Mark Sacchetti, Michiel M Van Oort) in Inhalation Aerosols: Physical and Biological Basis for Therapy (Anthony J. Hickey), 1996, Chapter 11, pp. 337-385.

Kawashima et al., "A New Powder Design Method to Improve Inhalation Efficiency of Pranlukast Hydrate Dry Powder Aerosols by Surface Modification with Hydroxypropylmethylcellulose Phthalate Nanospheres," *Pharmaceutical Research*, vol. 15, No. 11, pp. 1748-1752 (Nov. 1998).

US 5,849,884, 12/1998, Woiszwillo et al. (withdrawn)

* cited by examiner

SOLID PHARMACEUTICAL DISPERSIONS WITH ENHANCED BIOAVAILABILITY

This is a continuation of application Ser. No. 09/131,019, now abandoned, which was filed on Aug. 7, 1998, and which claimed priority under 35 USC 119(e) to U.S. Provisional Application No. 60/055,221, filed Aug. 11, 1997.

FIELD OF THE INVENTION

This invention relates to compositions of drugs that have increased aqueous concentration, to processes for preparing such compositions, and to methods of using such compositions. In particular, it relates to compositions comprising a spray dried dispersion of a sparingly soluble drug in hydroxypropylmethylcellulose acetate succinate.

BACKGROUND OF THE INVENTION

It is known in the pharmaceutical arts that low-solubility drugs often show poor bioavailability or irregular absorption, the degree of irregularity being affected by factors such as dose level, fed state of the patient, and form of the drug.

Solid dispersions of a drug in a matrix can be prepared by forming a homogeneous solution or melt of the drug and matrix material followed by solidifying the mixture by cooling or removal of solvent. Such dispersions have been known for more than two decades. Such solid dispersions of crystalline drugs often show enhanced bioavailability when administered orally relative to oral compositions comprising undispersed crystalline drug.

In general, it is known that the use of water-soluble polymers as the matrix material generally yields good results. Examples of water soluble polymers which have been employed include polyvinylpyrrolidone (PVP), hydroxypropyl methyl cellulose (HPMC), hydroxypropyl cellulose (HPC), methyl cellulose (MC), block copolymers of ethylene oxide and propylene oxide (PEO/PPO), and polyethyleneglycol (PEG). In a 1986 review of solid amorphous dispersions, see Ford, J. L., Pharm Acta. Helv., 61:3 (1986), criteria are set forth for choosing a suitable matrix, termed a "carrier" therein. The first and most important criterion listed therein is that the carrier "should be freely water soluble with intrinsic rapid dissolution properties." As a result of this view, which is currently widely held, the majority of reports of solid amorphous dispersions of drugs in polymers use polymers which rapidly dissolve in water or gastric fluid such as PVP, PEG, or other water-soluble polymers.

There have been a relatively small number of reports of using water insoluble polymers as the matrix material for solid amorphous dispersions, although in some cases such polymers are soluble in aqueous base. The clear focus of most of these reports is on achieving sustained release of the drug, as opposed to increasing bioavailability. For example, sodium carboxymethylcellulose (NaCMC) and hydroxypropylmethyl cellulose acetate succinate (HPMCAS), both polymers that are insoluble in water or gastric fluid but soluble in aqueous base, such as solutions containing sufficient base to have a pH of 6.5 or greater following dissolution of HPMCAS, have been used in an attempt to simultaneously encapsulate and form a dispersion of drug via a spray-drying process. See Wan et al., Drug Development and Industrial Pharmacy, 18:9, 997-1011 (1992). The authors attempted to form a dispersion of theophylline in HPMCAS by dispersing crystals of theophylline and particles of HPMCAS in water. Neither the drug nor the HPMCAS dissolved appreciably in the water. The resulting slurry was spray dried and resulted in a product (p.1009, line 11) consisting of long thin needle-like theophylline with scattered HPMCAS particles. The authors concluded (p.1010, line 5) that of the polymers studied, only HPMCAS was found unsuitable for their process. The authors state that the intent of the process was to retard rather than enhance the rate of release of drug. Indeed, for all polymers disclosed, in vitro tests showed drug concentrations that were the same or lower than that obtained with drug alone.

Miyajima et al., U.S. Pat. No. 4,983,593, disclose, inter alia, formulating HPMCAS with a drug designated as NZ-105. The patent disclosed that there is formed "a composition having a remarkably enhanced bioavailability and easily prepared into tablets, capsules, granules, powders, and the like . . . ." The patent teaches that the formulations can be prepared by dissolving NZ-105 and HPMCAS in an organic solvent and removing the solvent by means of vacuum-drying, spray-drying, freeze-drying, or the like, or by coating a filler such as an inorganic salt (e.g., calcium hydrogen phosphate) or a sugar (e.g., lactose, sucrose, and so forth) and the like by means of a fluidized bed granulation method, a centrifugal coating method, or a pan coating method to produce granules. The patent discloses that granules can also be prepared by adding a solvent to a filler and kneading the mixture followed by drying. All examples in the patent describe forming a dispersion of HPMCAS and NZ-105 by either (1) fluidized bed granulation by coating either calcium hydrogen phosphate particles or lactose crystals to form large particles up to 1400 μm in diameter or 2) vacuum drying with lactose to form a solid cake that is then pulverized to form a powdery material.

Nakamichi et al., U.S. Pat. No. 5,456,923, disclose, inter alia, a process for producing solid dispersions by passing a mixture of a drug and a polymer carrier through a twin screw compounding extruder. HPMCAS is mentioned as one polymer from among a group of suitable polymers which can be used.

U.S. Pat. No. 5,456,923 to Shogo et al discloses an extrusion method for making solid dispersions. HPMCAS is included in a list of polymeric materials, including materials such as starch or gelatin, that can be used as matrix materials.

Takeichi et al, Chem. Pharm. Bull, 38 (9), 2547-2551 (1990) attempted to use a solid dispersion of HPMCAS and uracil made by grinding in a ball mill to enhance rectal absorption, but concluded that uracil absorption was lower than for low molecular weight matrix materials such as sodium caprate. The use of HPMCAS was not recommended.

Baba, et al, Chem. Pharm. Bull, 38 (9), 2542-2546 (1990) made ground mixtures of uracil and HPMCAS along with 50 other matrix materials. Although some enhancement (about a factor of 2) in the dissolution of uracil was observed in the co-ground HPMCAS material relative to a simple mixture of crystalline drug and HPMCAS, the enhancement decreased as the polymer-to-drug ratio was increased. This led the researchers to conclude that HPMCAS adsorbed on the surface of the uracil thereby hindering the dissolution of uracil. Its use was not recommended.

T. Yamaguchi et al, Yakuzaigaku, 53 (4), 221-228 (1993) prepared solid amorphous dispersions of 4"-0-(4-methoxyphenyl)acetyltylosin (MAT) in HPMCAS as well as CMEC. Dissolution tests at pH 4.0 showed supersaturated concentrations of MAT 9-fold that of crystalline MAT with HPMCAS dispersions. This concentration was comparable to that obtained with the dissolution of amorphous drug alone. However, the presence of HPMCAS sustained the supersaturation longer than the amorphous drug alone. The authors report that even better results were obtained with the CMEC dispersions, however, causing the authors to conclude that CMEC is the preferred dispersion matrix.

SUMMARY OF THE INVENTION

In a first aspect, this invention provides a composition comprising a spray dried solid dispersion, which dispersion comprises a sparingly water-soluble drug and hydroxypropylmethylcellulose acetate succinate (HPMCAS), said dispersion providing a maximum concentration of said drug in a use environment that is higher by a factor of at least 1.5 relative to a control composition comprising an equivalent quantity of undispersed drug.

In another aspect, this invention provides a method of increasing the bioavailability of a sparingly-soluble drug, comprising administering said drug in a composition comprising a spray dried solid dispersion, which dispersion comprises said drug and hydroxypropylmethylcellulose acetate succinate (HPMCAS), said dispersion providing a concentration of said drug in a use environment that is higher by a factor of at least 1.5 relative to a composition comprising an equivalent quantity of undispersed drug.

In another aspect this invention provides a process for making a spray dried solid dispersion comprising A. forming a solution comprising (i) HPMCAS, (ii) a sparingly water-soluble drug, and (iii) a solvent in which both (i) and (ii) are soluble; and B. spray drying said solution, thereby forming spray dried particles having an average diameter less than 100 μm. In a preferred embodiment the concentration of drug in the solvent is less than 20 g/100 g of solvent with a total solids content less than 25 weight %, preferably less than 15 weight %. In another preferred embodiment the spray drying is conducted under conditions whereby the droplets solidify in less than 20 seconds.

The sparingly soluble drugs suitable for use in this invention can be crystalline or amorphous in their undispersed state. A crystalline drug, once dispersed, is substantially non-crystalline as determined by scanning calorimetry or x-ray diffraction.

The term "drug" in this specification and the appended claims is conventional, denoting a compound having beneficial prophylactic and/or therapeutic properties when administered to an animal, including humans.

A use environment can be either the in vivo environment of the gastrointestinal tract of an animal, particularly a human, or the in vitro environment of a test solution, an example being "MFD" (for model fasted duodenal) solution. A dispersion (or a composition comprising a dispersion) can correspondingly be tested in vivo or, more conveniently, tested in vitro as further disclosed and discussed below to ascertain whether it is within the scope of the invention.

In a preferred embodiment the drug/HPMCAS spray dried dispersion itself consists essentially of sparingly soluble drug and HPMCAS. Other components can be included in the dispersion if they are inert in the sense that they do not adversely affect the maximum supersaturated concentration (MSSC) of drug achievable with the dispersion in a use environment. Components which do affect the MSSC can also be included, so long as they do not adversely affect (i.e., by lowering) the MSSC materially, meaning that all such components in the dispersion do not lower the MSSC by more than 20% relative to a spray dried dispersion not containing such components. Components which do not affect, or in fact improve MSSC, can be included in any amount. Generally, the amount of HPMCAS and drug in the dispersion, not counting any residual solvent, should be greater than 75% by weight.

In vitro, a composition of matter comprising a spray-dried dispersion of a sparingly soluble drug in HPMCAS is within the scope of the invention if, when said dispersion is dissolution tested, the maximum supersaturated concentration of said drug achievable with said dispersion is higher by a factor of at least 1.5 relative to the equilibrium concentration achieved by dissolution testing a composition comprising an equivalent quantity of undispersed drug. "Dissolution testing" refers to a repeatable, standardized test which employs, as a test medium, an aqueous liquid in which HPMCAS is soluble. Generally, aqueous liquids (i.e., water solutions) having a pH of 6 and higher following dissolution of HPMCAS are satisfactory. Of course, the test should also be capable of reproducibly evaluating equilibrium and/or supersaturated concentrations of a drug. A convenient dissolution test employs MFD solution as a test medium in a USP-2 apparatus as described in United States Pharmacopoeia XXIII (USP) Dissolution Test Chapter 711, Apparatus 2. Solution volume, paddle speed and temperature are not considered to be critical so long as test dispersions and controls are tested under like or standardized conditions, for example 500 mL of MFD, paddle speed of 100 rpm, and 37° C. Other values for these parameters can be employed so long as they are maintained constant such that the concentrations being measured are measured under the same conditions. Dissolution testing is typically conducted by comparing a test composition comprising a drug/HPMCAS dispersion with a control composition identical except that it contains pure drug in its equilibrium—either crystalline or amorphous—form. The control composition is typically the same as the test composition but for the inclusion of HPMCAS. The HPMCAS can simply be omitted altogether and just the drug added to the remainder of the composition, or the HPMCAS can be replaced by an equal amount of inert, non-adsorbing solid diluent such as microcrystalline cellulose. Thus, the control composition should also contain any excipients and/or other components, in the amounts such other components are contained by the test composition.

Preferred dispersions are those for which the in vitro (e.g., MFD) drug concentration falls to no less than 25% of the MSSC during the 15 minutes after MSSC is reached, preferably 30 minutes after MSSC is reached.

In the same manner, a composition of matter comprising a spray-dried dispersion of a sparingly soluble drug in HPMCAS is within the scope of the invention if, when a composition comprising said dispersion is tested in vivo, the Cmax achieved with said composition is higher by a factor of at least 1.25 (i.e., 25% higher) relative to the Cmax achieved with a composition comprising an equivalent quantity of undispersed drug. As indicated above, Cmax is an abbreviation for the maximum drug concentration in serum or plasma of the test subject. In vivo testing protocols can be designed in a number of ways. By measuring the Cmax for a population to which the test composition has been administered and comparing it with the Cmax for the same population to which the control has also been administered, the test composition can be evaluated.

Compositions according to the invention exhibit at least a factor of 1.25 improvement in AUC, which is a determination of the area under a curve (AUC) plotting the serum or plasma concentration of drug along the ordinate (Y-axis) against time along the abscissa (X-axis). Generally, the values for AUC represent a number of values taken from all the subjects in a patient test population and are, therefore, mean values averaged over the entire test population. By measuring the AUC for a population to which the test composition has been administered and comparing it with the AUC for the same population to which the control has been administered, the test composition can be evaluated. AUC's are well understood, frequently used tools in the pharmaceutical arts and have been extensively described, for example in "Pharmacokinetics Processes and Mathematics", Peter E. Welling, ACS Monograph 185; 1986. AUCs for this invention were typically determined over a period of 48 or 72 hours starting from the time the dispersion or control was first administered.

Thus, a composition is within the scope of the invention if it exhibits in vivo either a Cmax or an AUC that is 1.25 times the corresponding Cmax or AUC exhibited by a composition comprising an equivalent quantity of undispersed drug. In a preferred embodiment, compositions according to the invention, in addition to displaying at least a factor of 1.25 improvement in Cmax as discussed above, also exhibit at least a factor of 1.25 improvement in AUC.

Cmax and AUC can be determined in humans or a suitable animal model, such as dogs.

A "sparingly-soluble drug" as employed above applies to drugs which are essentially totally water-insoluble or poorly water-soluble. More specifically, the term applies to any beneficial therapeutic agent which has a dose (mg) to aqueous solubility (mg/ml) ratio greater than 100 ml, where the drug solubility is that of the neutral (e.g., free base or free acid) form in unbuffered water. This definition includes but is not limited to drugs that have essentially no aqueous solubility (less than 1.0 μg/ml) since it has been determined that the invention has benefit for such drugs. In general, the drug is dispersed in the HPMCAS such that most of the drug is not present in crystalline form greater than about 0.1 μ in diameter. The drug may be present in amorphous drug-rich domains as long as the drug will dissolve to form supersaturated solutions in in vitro tests disclosed hereinafter. However, it is generally preferred for the drug to be molecularly dispersed such that there is little or no drug present as separate amorphous domains.

For the purposes of this invention, a "sparingly soluble amorphous drug" is a drug that, in its amorphous state, is sparingly soluble as described above and also, upon storage for 30 days at 30° C. shows no tendency to crystallize as measured by calorimetric techniques or powder x-ray diffraction. An example of such a drug is N-tert-butyl-2-{3-[3-(3-chloro-phenyl)-unreido]-8-methyl-2-oxo-5-phenyl-2,3,4,5-tetrahydrobenxo[b]azepin-1-yl}-acetamide, which has an aqueous solubility (pH 6.5) of less than 3.0 μg/ml and a broad melting range of 115° to 137° C.

A preferred class of compounds for use in this invention is glycogen phosphorylase inhibitors, such as those disclosed in PCT/IB95/00443, published internationally as WO96/39385 on Dec. 12, 1996. Specific compounds include those having the structures

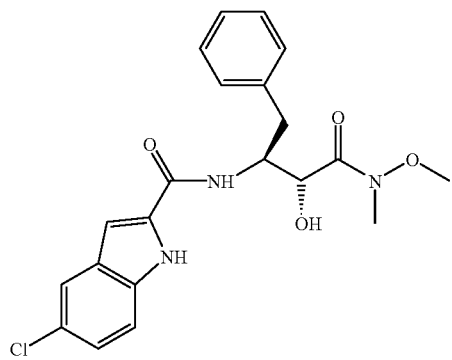

and

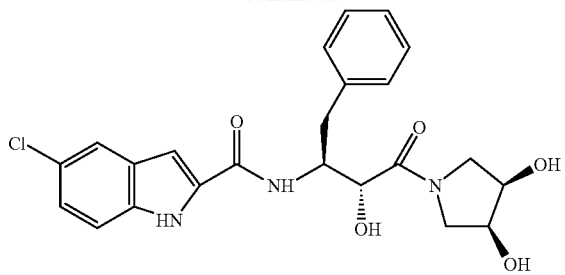

Another preferred class of compounds for use in this invention is 5-lipoxygenase inhibitors, such as those disclosed in PCT/JP94/01349, published as WO 95/05360. A preferred compound has the structure

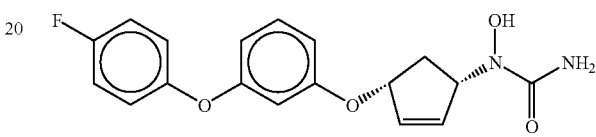

Another preferred class of compounds for use in this invention is corticotropic releasing hormone (CRH) inhibitors such as those disclosed in PCT/IB95/00439 published as WO95/33750. Specific compounds include those having the following structure:

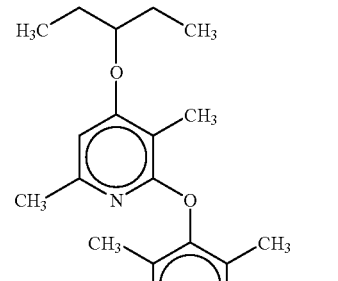

and

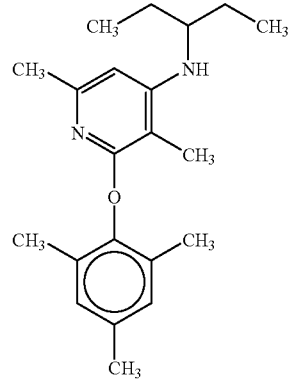

Another preferred class of compounds is antipschotics. A particularly preferred compound is ziprasidone.

Other preferred compounds include griseofulvin, nifedipine, and phenytoin.

The specific compounds and classes disclosed above are understood to include all forms thereof, including pharmaceutically acceptable salts, hydrates, polymorphs, and steroisomers.

"MFD" is an acronym meaning "model fasted duodenal" fluid which is employed as an in vitro test medium for purposes of determining whether a particular drug/HPMCAS dispersion falls within the scope of this invention. The MFD test medium allows testing in more convenient in vitro conditions and environment by virtue of mimicking an in vivo environment. For purposes of this invention, MFD is water which is 82 mM (millimolar) in NaCl, 20 mM in $Na_2HPO_4$, 47 mM in $KH_2PO_4$, 14.7 mM in sodium taurocholate and 2.8 mM in 1-palmitoyl-2-oleoyl-sn-glycero-3-phosphocholine to yield a solution pH of about 6.5 and osmotic pressure of about 290 mOsm/kg. MFD is described in greater detail below.

The term "HPMCAS" as used herein refers to a family of cellulose derivatives that can have (1) two types of ether substituents, methyl and/or 2-hydroxypropyl and (2) two types of ester substituents, acetyl and/or succinyl. It is referred to in scientific literature as O-(2-hydroxypropyl)-O-methyl-cellulose acetate succinate. The degree of substitution for each of the four general types just noted can be varied over a wide range to effect the chemical and physical properties of the polymer. This versatility of HPMCAS allows its structure to be optimized to obtain good performance with a particular drug of interest. HPMCAS can be synthesized as noted below or purchased commercially. Three examples of commercially available HPMCAS include Shin-Etsu AQOAT®-LF, Shin-Etsu AQOAT®-MF, and Shin-Etsu AQOAT®-HF. All three of these polymers are manufactured by Shin-Etsu Chemical Co., Ltd. (Tokyo, Japan), and all three have proven to be suitable for use in practicing the present invention. The specific grade that yields the best performance for obtaining and sustaining supersaturation in in vitro tests and obtaining high bioavailability in vivo, varies depending on the specific chemical and physical properties of the drug to be delivered. A preferred mean weight average molecular weight range for HPMCAS is 10,000 to one million daltons, preferably 10,000 to 400,000 daltons, as determined using polyethylene oxide standards.

Drugs which are preferred for use in this invention include those which have a dose to aqueous solubility greater than 100, where the aqueous solubility is measured in unbuffered water. For ionizable compounds, the appropriate solubility is that of the free base, free acid, or zwitterion, i.e., the solubility of the neutral form. Drugs which will particularly benefit from formulation in spray-dried HPMCAS dispersions of this invention include those drugs which have a dose to aqueous solubility ratio greater than 500. Examples of such drugs are disclosed in the examples herein.

In general, when "solubility" is referred to, aqueous solubility is intended unless otherwise indicated.

It has been determined that a spray dried solid dispersion of a sparingly-soluble drug in HPMCAS has unique properties making it broadly useful for preparing oral dosage forms. While not wishing to be bound by any particular theory or mechanism, it is believed that in order for a solid amorphous dispersion of a drug in a matrix material to function optimally in improving the bioavailability of sparingly-soluble drugs, the matrix material must generally provide the following functions:

1. disperse the drug, thereby preventing or retarding the rate of crystallization in the solid state,
2. dissolve in vivo, thereby allowing the drug to be released to the gastrointestinal tract,
3. inhibit the precipitation or crystallization of aqueous dissolved drug.

It has been determined that a spray-dried solid dispersion of a sparingly soluble drug in HPMCAS is superior insofar as above functions 1-3 are concerned, and that such dispersions provide unexpectedly good formulatability and solubility.

If a drug does not have a strong tendency to crystallize from the amorphous solid state, then only the latter two functions are required. When a solid amorphous dispersion of a drug in HPMCAS is prepared, the drug will, either prior to or following dissolution of the drug HPMCAS dispersion, reach a concentration substantially higher than the equilibrium solubility of the drug alone. That is, the drug reaches a supersaturated concentration, and this supersaturated concentration will be maintained for a relatively long time period. HPMCAS functions well in all three respects noted above such that it is unique among known matrix materials in its ability to inhibit the precipitation or crystallization of a broad range of sparingly soluble drugs from a supersaturated solution. Further, and again without wishing to be bound by theory, it is believed that spray drying effects rapid solvent removal so that crystallization of drug and HPMCAS is largely prevented, or at least minimized relative to other methods of forming dispersions, including other solvent removal processes such as rotary evporation. In addition, in many cases spray drying effects removal of solvent sufficiently fast that even phase separation of amorphous drug and HPMCAS is largely prevented or minimized. Thus, HPMCAS and spray drying afford a better, more truly homogeneous dispersion in which the drug is more efficiently dispersed in the polymer. Increased efficiency of dispersion from spray drying gives, relative to other methods of making dispersions, a higher drug concentration in in vitro tests.

Surprisingly, a solid amorphous dispersion comprising a spray dried mixture of HPMCAS and a sparingly soluble amorphous drug, that is, one that shows little tendency to crystallize from its amorphous state can benefit from this invention. Solid dispersions of such drugs in HPMCAS surprisingly show high degrees and durations of supersaturation in in vitro dissolution tests relative to compositions comprising undispersed amorphous drug. This finding runs contrary to conventional wisdom in that attempts to enhance the bioavailability of drugs by making solid amorphous dispersions have been directed exclusively toward drugs that, in their pure state, are crystalline or, if made amorphous, spontaneously progress toward the crystalline state. In fact, in the course of developing an appropriate matrix material, two in vitro screening methods (see Examples 2 and 3) have been developed and employed to screen a wide range of drugs. The results of these in vitro screening tests, based on drug levels in MFD solution, are predictive of in vivo bioavailability based on drug levels in blood when dosed orally to dogs or humans. Results obtained from these screening tests support the surprising finding that amorphous dispersions of hydrophobic drugs that are either amorphous in their pure state or show little tendency to be crystalline (e.g., crystal forces are low) also have greatly improved degrees and durations of supersaturation in in vitro dissolution tests relative to amorphous drug alone. This finding is surprising in that conventional wisdom holds that the function of dispersing a drug in a matrix material is to prevent or retard its crystallization, and thus that using such matrices should do little to increase the solubility of a drug which is already non-crystalline.

DETAILED DESCRIPTION OF THE INVENTION AND PREFERRED EMBODIMENTS

Figure 1:
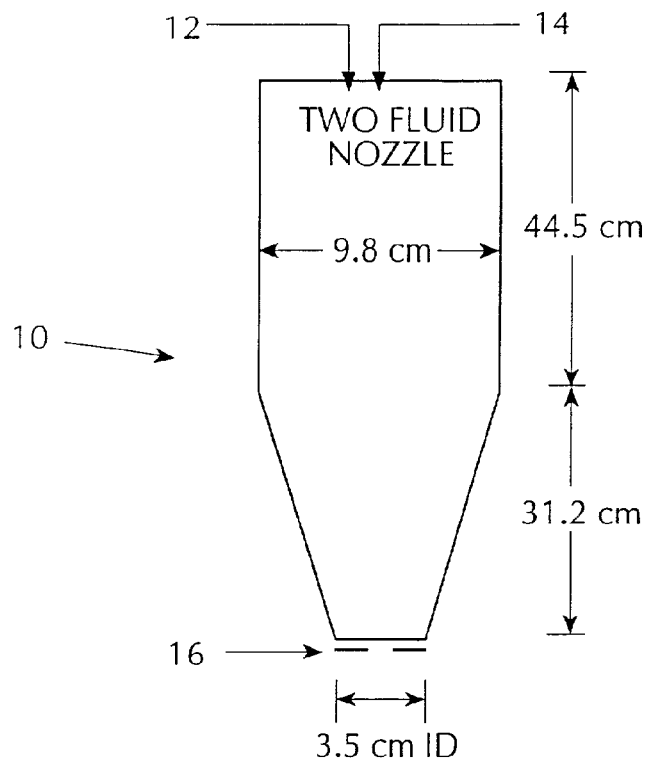
FIG. 1 is a schematic diagram of a mini spray drying apparatus used for the examples.

Synthesis of HPMCAS can be conducted by treating O-(hydroxypropyl)-O-methylcellulose with acetic anhydride and succinic anhydride, as set forth in Tezuka et al, Carbohydrate Research 222(1991)255-259 and in Onda et al, U.S. Pat. No. 4,385,078, the teachings of which are incorporated herein by reference. Although such derivatives of cellulose are often considered in the literature as simply having varying average amounts of the four substituents attached to the three hydroxyl groups on each of the glucose repeat units of cellulose, $^{13}$C-NMR research suggests that most of the hydroxyl groups initially present on the 2-hydroxypropyl groups are substituted by methyl, acetyl, succinyl, or a second 2-hydroxypropyl group, see U.S. Pat. No. 4,385,078. Although essentially any degree of substitution of the various groups can be used as long as the resulting polymer is soluble at the pH of the small intestine, e.g., pH 6 to 8, the amounts of the substituents methoxy, hydroxypropoxy, acetyl, and succinyl, are generally in the range of 10 to 35 wt %, 3 to 15 wt %, 3 to 20 wt %, and 2 to 30 wt %, respectively. Preferably, the amounts of the substituents are 15 to 30 wt %, 4 to 11 wt %, 4 to 15 wt %, and 3 to 20 wt %, respectively. Alternatively, HPMCAS may easily be purchased from a number of commercial suppliers.

The amount of HPMCAS relative to the amount of drug present in the dispersions of the present invention can vary widely from a drug:polymer weight ratio of 1 to 0.2 to 1 to 100. However, in most cases it is preferred that the drug to polymer ratio is greater than 1 to 20 and less than 1 to 0.4. The minimum drug:polymer ratio that yields satisfactory results varies from drug to drug and is best determined in the in vitro dissolution tests described below.

Although the key ingredients present in the solid amorphous compositions of the present invention are simply the drug to be delivered and HPMCAS, the inclusion of other excipients in the dispersion may be useful and even preferred. For example, polymers other than HPMCAS that are soluble in aqueous solutions over at least a portion of the range pH 1.0 and 8.0 can be included in the dispersion along with HPMCAS. For example, it has been found that amorphous dispersions of drug and conventional matrix materials such as PVP, HPC, or HPMC can be formed and then triturated with HPMCAS and still have, for some drugs, superior performance relative to the same dispersions without HPMCAS. In such cases, it appears that, whether the drug is crystalline or amorphous, HPMCAS may have as its primary benefit inhibition of the precipitation or crystallization of drug from supersaturated solution. Included as a preferred embodiment of this invention are dispersions in which drug, HPMCAS, and one or more additional polymers are co-spray dried, wherein drug and HPMCAS constitute not more than 75% of the dispersion.

Another type of excipient useful as a component of the dispersions herein is a surface-active agent such as a fatty acid and alkyl sulfonate; commercial surfactants such as those sold under tradenames such as benzethanium chloride (Hyamine® 1622, available from Lonza, Inc., Fairlawn, N.J., docusate sodium (available from Mallinckrodt Spec. Chem., St. Louis, Mo., and polyoxyethylene sorbitan fatty acid esters (Tween®, available from ICI Americas Inc, Wilmington, Del., Liposorb® P-20, available from Lipochem Inc, Patterson, N.J., and Capmul® POE-0, available from Abitec Corp., Janesville, Wis.), and natural surfactants such as sodium taurocholic acid, 1-palmitoyl-2-oleoyl-sn-glycero-3-phosphocholine, lecithin, and other phospholipids and mono- and diglycerides. Such materials can advantageously be employed to increase the rate of dissolution by facilitating wetting, thereby increasing the maximum drug concentration and the degree of supersaturation attained, and also to inhibit crystallization or precipitation of drug by interacting with dissolved drug by mechanisms such as complexation, formation of inclusion complexes, formation of micelles or adsorbing to the surface of solid drug, crystalline or amorphous. These surface active agents may comprise up to 25% of the spray-dried dispersion.

Addition of pH modifiers such as acids, bases, or buffers can also be beneficial. pH modifiers can advantageously serve to retard the dissolution of the dispersion (e.g., acids such as citric acid or succinic acid) or, alternatively, to enhance the rate of dissolution of the dispersion (e.g., bases such as sodium acetate or amines). Addition of conventional matrix materials, surface active agents, fillers, disintegrants, or binders may be added as part of the dispersion itself, added by granulation via wet or mechanical or other means. When such additives are included as part of the dispersion itself, they can be mixed with drug and HPMCAS in the spray drying solvent, and may or may not dissolve along with the drug and HPMCAS prior to forming the dispersion by spray drying. These materials may comprise up to 25% of the drug/HPMCAS/additive dispersion.

In addition to drug and HPMCAS (and other polymers as discussed immediately above), other conventional formulation excipients can be employed in the compositions of this invention, including those excipients well known in the art. Generally, excipients such as fillers, disintegrating agents, pigments, binders, lubricants, flavorants, and so forth can be used for customary purposes and in typical amounts without affecting the properties of the compositions. These excipients are utilized after the HPMCAS/drug dispersion has been formed, in order to formulate the dispersion into tablets, capsules, suspensions, powders for suspension, creams, transdermal patches, and the like.

The term spray-drying is used conventionally and broadly refers to processes involving breaking up liquid mixtures into small droplets (atomization) and rapidly removing solvent from the mixture in a container (spray-drying apparatus) where there is a strong driving force for evaporation of solvent from the droplets. The strong driving force for solvent evaporation is generally provided by maintaining the partial pressure of solvent in the spray-drying apparatus well below the vapor pressure of the solvent at the temperature of the drying droplets. This is accomplished by either (1) maintaining the pressure in the spray-drying apparatus at a partial vacuum (e.g., 0.01 to 0.50 atm); (2) mixing the liquid droplets with a warm drying gas; or (3) both. For example, a solution of drug and HPMCAS in acetone can be suitably spray-dried by spraying the solution at a temperature of 50° C. (the vapor pressure of acetone at 50° C. is about 0.8 atm) into a chamber held at 0.01 to 0.2 atm total pressure by connecting the outlet to a vacuum pump. Alternatively, the acetone solution can be sprayed into a chamber where it is mixed with nitrogen or other inert gas at a temperature of 80° C. to 180° C. and a pressure of 1.0 to 1.2 atm.

Generally, the temperature and flow rate of the drying gas is chosen so that the HPMCAS/drug-solution droplets are dry enough by the time they reach the wall of the apparatus that they are essentially solid, so that they form a fine powder and do not stick to the apparatus wall. The actual length of time to achieve this level of dryness depends on the size of the droplets. Droplet sizes generally range from 1 µm to 500 µm in diameter, with 5 to 100 µm being more typical. The large surface-to-volume ratio of the droplets and the large driving force for evaporation of solvent leads to actual drying times of a few seconds or less. This rapid drying is critical to the particles maintaining a uniform, homogeneous composition instead of separating into drug-rich and polymer-rich phases. Such dispersions which have a homogeneous composition can be considered solid solutions and may be supersaturated in drug. Such homogeneous dispersions are preferred in that the MSSC value obtained when a large amount of drug is dosed can be higher for such dispersions relative to dispersions for which at least a portion of the drug is present as a drug-rich amorphous or crystalline phase. Solidification times should be less than 20 seconds, preferably less than 5 seconds, and more preferably less than 2 seconds. In general, to achieve this rapid solidification of the drug/polymer solution, it is preferred that the size of droplets formed during the spray drying process are less than 100 µm in diameter, preferably less than 50 µm in diameter, and more preferably less than 25 µm in diameter. The resultant solid particles thus formed are generally less than 100 µm in diameter, preferably less than 50 µm in diameter, more preferably less than 25 µm in diameter.

Following solidification, the solid powder may stay in the spray-drying chamber for 5 to 50 seconds, further evaporating solvent from the solid powder. The final solvent content of the solid dispersion as it exits the dryer should be low, since this reduces the mobility of drug molecules in the dispersion, thereby improving its stability. Generally, the residual solvent content of the dispersion should be less than 10 wt % and preferably less than 2 wt %.

The dispersions can then be post-processed to prepare them for administration using methods known in the art such as roller compaction, fluid bed agglomeration, or spray coating.

Spray-drying processes and spray-drying equipment are described generally in Perry's *Chemical Engineers' Handbook*, Sixth Edition (R. H. Perry, D. W. Green, J. O. Maloney, eds.) McGraw-Hill Book Co. 1984, page 20-54 to 20-57. More details on spray-drying processes and equipment are reviewed by Marshall ("Atomization and Spray-Drying," Chem. Eng. Prog. Monogr. Series, 50 [1954] 2).

The solution spray-dried to form the HPMCAS/drug dispersion can contain only drug and HPMCAS in a solvent. Typically, the ratio of drug to HPMCAS in the solution ranges from 1 to 0.2 to 1 to 100 and preferably ranges from 1 to 0.4 to 1 to 20. However, when the drug dose is low (less than 20 mg), the drug-to-HPMCAS ratio can be even higher than 20. Essentially, solvents suitable for spray-drying can be any organic compound in which the drug and HPMCAS are mutually soluble. Preferably, the solvent is also volatile with a boiling point of 150° C. or less. Preferred solvents include alcohols such as methanol, ethanol, n-propanol, iso-propanol, and butanol; ketones such as acetone, methyl ethyl ketone and methyl iso-butyl ketone; esters such as ethyl acetate and propylacetate; and various other solvents such as acetonitrile, methylene chloride, toluene, and 1,1,1-trichloroethane. Lower volatility solvents such as dimethyl acetamide or dimethylsulfoxide can also be used. Mixtures of solvents can also be used, as can mixtures with water as long as the polymer and HPMCAS are sufficiently soluble to make the spray-drying process practical.

Spray-dried solutions and the resulting dispersions can also contain various additives that aid in the stability, dissolution, tableting, or processing of the dispersion. As mentioned previously, examples of such additives include: surfactants, pH-controlling substances (e.g., acids, bases, buffers), fillers, disintegrants, or binders. Such additives can be added directly to the spray-drying solution such that the additive is dissolved or suspended in the solution as a slurry. Alternatively, such additives can be added following the spray-drying process to aid in forming the final dosage form.

In a further aspect this invention provides an in vitro test for evaluating the performance of HPMCAS candidate dispersion compositions, thereby allowing the identification of dispersion compositions that will yield good in vivo bioavailability of drug when taken orally. It has been determined that in vitro dissolution of a dispersion in model-fasted duodenal (MFD) solution is a good indicator of in vivo performance and bioavailability. In particular, a candidate dispersion can be dissolution tested by adding it to MFD solution and agitating to assist in dissolution. In this test, the amount of dispersion is chosen such that if all drug dissolves, a 1.5-fold or greater supersaturated solution is obtained. A dispersion is within the scope of this invention if the maximum supersaturated concentration of drug exceeds, by a factor of at least 1.5, the equilibrium concentration of a control composition comprising an equivalent quantity of undispersed drug. As previously discussed, the comparison composition is conveniently the undispersed drug alone (e.g., pure drug in its equilibrium state—either crystalline or amorphous) or the undispersed drug plus a weight of inert diluent equivalent to the weight of HPMCAS in the test composition. Preferably the supersaturated concentration of drug achieved with the test dispersion exceeds the equilibrium drug concentration by a factor of at least three, and most preferably by a factor of at least five.

A typical test can be conducted by (1) dissolving a sufficient quantity of control composition, typically the candidate drug alone, to achieve equilibrium drug concentration; (2) dissolving a sufficient quantity of test dispersion to achieve a maximum supersaturated drug concentration; and (3) determining whether the supersaturated concentration exceeds the equilibrium concentration by a factor of at least 1.5. The concentration of dissolved drug is typically measured as a function of time by sampling the solution and plotting concentration vs. time so that the concentration maximum can be ascertained. For purposes of avoiding drug particulates which would give an erroneous determination in the test, the test solution is either filtered or centrifuged. "Dissolved drug" is typically taken as that material that either passes a 0.45 µm syringe filter or, alternatively, that material that remains in the supernatant following centrifugation. Filtration can be conducted using a 13 mm, 0.45 µm polyvinylidine difluoride syringe filter sold by Scientific Resources under the trademark Titan®. Centrifugation is typically carried out in a polypropylene microcentrifuge tube by centrifuging at 13,000 G for 60 seconds using any centrifuge suitable for the purpose. Other similar filtration or centrifugation methods can be employed and useful results obtained. For example, using other types of microfilters may yield values somewhat higher or lower (plus or minus 10 to 40%) than that obtained with the filter specified above but will still allow identification of suitable dispersions.

Dispersions can also be tested in dogs as follows:

Beagle dogs (typically n=4-6) that have been fasted the previous day are administered the formulation in the fasted or fed state (fasted state: no food is allowed until after an 8 hr blood sample; fed state: a meal of 14 g of dry dog food and 8 g of olive oil (this meal imitates the high fat "FDA breakfast") immediately before dosing test or control composition, and regular rations after the 8 hr sample).

The test and control formulations are administered, via oral gavage in water or 0.2% aqueous polysorbate 80 to aid in wetting, through PE205 tubing attached to a syringe. Dogs are returned to metabolism cages with normal access to water. Alternatively, dosing may be via capsules or tablets, with the provision that the test and control formulations be identical, except for the presence or absence of HPMCAS.

Blood samples are taken from the jugular vein using a 10 ml disposable syringe with a 20 gauge needle at 0.5, 1, 1.5, 2, 3, 4, 6, 8 (and occasionally 12 hr) hours post dose. Other sampling times may be used with the conditions that $T_{max}$ is bracketed by the sampling intervals and that an accurate AUC may be calculated. Samples are immediately transferred to clean glass culture tubes containing heparin. Samples are centrifuged at room temperature at 3000 rpms for 5 minutes. Plasma is transferred to clean glass 1 dram vials using a 5¼" pasteur pipette. Plasma samples are frozen on dry ice and stored in a laboratory freezer until assayed by HPLC.

From plasma or serum drug concentrations, typical pharmacokinetic parameters, such as $C_{max}$, $T_{max}$ and AUC are calculated for each dog, and then averaged for the test population.

Dispersions can be tested in vivo in humans as follows. In a crossover design, 4 or more healthy human subjects are dosed with a suspension of crystalline drug (or amorphous drug if the drug does not crystallize) or a suspension of drug/HPMCAS spray-dried dispersion. Blood samples are taken before dosing and at a variety of times post-dosing, with the number and temporal distribution of sampling times chosen to bracket $T_{max}$ and permit accurate measurement of AUC. Drug concentration in plasma or serum is measured by an appropriate assay, and $C_{max}$, $T_{max}$, and AUC are determined. A dispersion of this invention is a spray-dried drug/HPMCAS dispersion which, when tested in an animal species:

(a) exhibits a drug Cmax which is greater than 1.25-fold the $C_{max}$ determined after dosing crystalline drug alone (or amorphous drug if the drug does not crystallize), or (b) exhibits a drug AUC which is greater than 1.25-fold the AUC determined after dosing crystalline drug alone (or amorphous drug if the drug does not crystallize).

Preferred drug/HPMCAS dispersions are those which satisfy both the (a) and (b) criteria above.

Compositions of this invention can be used in a wide variety of forms for administration of drugs orally. Exemplary dosage forms are powders or granules that can be taken orally either dry or reconstituted by addition of water to form a paste, slurry, suspension or solution; tablets, capsules, or pills. Various additives can be mixed, ground, or granulated with the compositions of this invention to form a material suitable for the above dosage forms. Potentially beneficial additives fall generally into the following classes: other matrix materials or diluents, surface active agents, drug complexing agents or solubilizers, fillers, disintegrants, binders, lubricants, and pH modifiers (e.g., acids, bases, or buffers).

Examples of other matrix materials, fillers, or diluents include lactose, mannitol, xylitol, microcrystalline cellulose, calcium diphosphate, and starch.

Examples of surface active agents include sodium lauryl sulfate and polysorbate 80.

Examples of drug complexing agents or solubilizers include the polyethylene glycols, caffeine, xanthene, gentisic acid and cylodextrins.

Examples of disintegrants include sodium starch gycolate, sodium alginate, carboxymethyl cellulose sodium, methyl cellulose, and croscarmellose sodium.

Examples of binders include methyl cellulose, microcrystalline cellulose, starch, and gums such as guar gum, and tragacanth.

Examples of lubricants include magnesium stearate and calcium stearate.

Examples of pH modifiers include acids such as citric acid, acetic acid, ascorbic acid, lactic acid, aspartic acid, succinic acid, phosphoric acid, and the like; bases such as sodium acetate, potassium acetate, calcium oxide, magnesium oxide, trisodium phosphate, sodium hydroxide, calcium hydroxide, aluminum hydroxide, and the like, and buffers generally comprising mixtures of acids and the salts of said acids. At least one function of inclusion of such pH modifiers is to control the dissolution rate of the drug, matrix polymer, or both, thereby controlling the local drug concentration during dissolution. In some cases it has been determined that the MSSC values for some drugs are higher when the solid amorphous drug dispersion dissolves relatively slowly rather than fast, e.g., over 60 to 180 minutes rather than less than 60 minutes.

As was stated earlier, additives may be incorporated into the solid amorphous dispersion during or after its formation.

In addition to the above additives or excipients, use of any conventional materials and procedures for formulation and preparation of oral dosage forms using the compositions of this invention known by those skilled in the art are potentially useful.

Other features and embodiments of the invention will become apparent by the following examples which are given for illustration of the invention rather than limiting its intended scope. In the examples, reference is made to a mini spray dryer (schematically illustrated in FIG. 1) and to a micro spray dryer, schematically illustrated in FIG. 2. These spray dryers were adapted from commercially available spray dryers sold by NIRO to downsize them to a size suitable for laboratory scale production of spray dried drug products.

In the Examples, "mgA" is an acronym for "milligrams of active drug", i.e., the non-salt free base or free acid if the compound is ionizable. "pgA" similarly means micrograms of active drug.

The mini spray-dryer shown in FIG. 1 consists of an atomizer in the top cap of a vertically oriented stainless steel pipe shown generally as 10. The atomizer is a two-fluid nozzle (Spraying Systems Co. 1650 fluid cap and 64 air cap) where the atomizing gas is nitrogen delivered through line 12 to the nozzle at 100° C. and a flow of 15 gm/min, and a test solution to be spray dried is delivered through line 14 to the nozzle at room temperature and a flow rate of 1.0 gram/min using a syringe pump (Harvard Apparatus, Syringe Infusion Pump 22, not shown). Filter paper 16 with a supporting screen (not shown) is clamped to the bottom end of the pipe to collect the solid spray-dried material and allow the nitrogen and evaporated solvent to escape.

Figure 2:
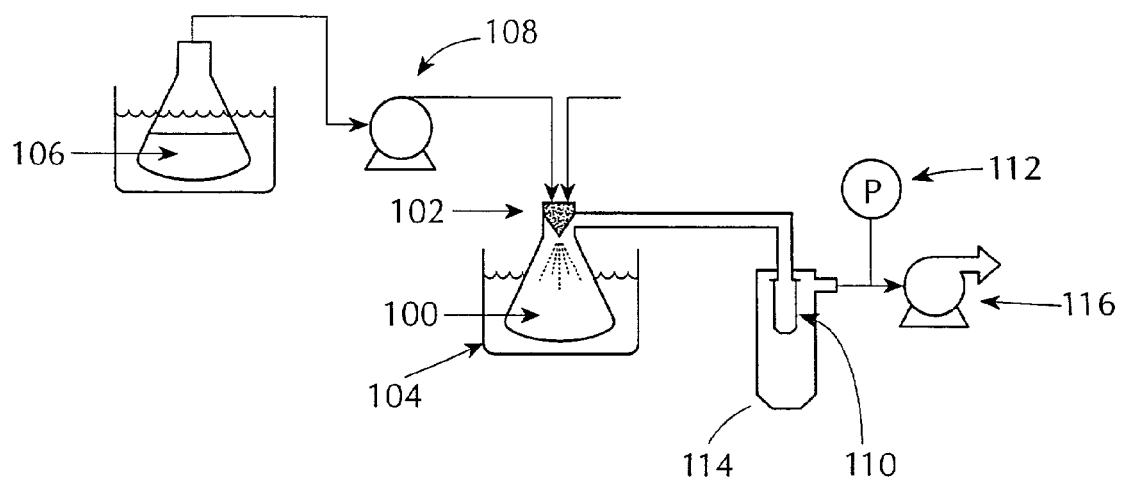
FIG. 2 is a schematic diagram of a micro spray drying apparatus used for the examples.

The micro spray dryer shown in FIG. 2 consists of an atomizer 102 in the top of a vacuum flask 100 kept at 40° C. by a water bath 104. Atomizer 102 is a two-fluid spray nozzle (NIRO Aeromatic, 2.7 mm ID air cap, 1.0 mm ID fluid cap) where the atomizing gas is nitrogen delivered to the nozzle at ambient temperature and at 20 psi, and the drug/polymer test solution 106 is delivered to nozzle 102 at 40° C. at a flow rate of 1.0 gm/min using a peristaltic pump 108 (Masterflex, model 7553-60, with pump head #7013-20, and Norprene tubing #6404-13). Microporous cellulose extraction thimble 110 (Whatman Filter Co.) is mounted in a vacuum trap 114 to collect the solid spray-dried material, and a vacuum of 400 mbar (monitored by vacuum gauge 112) is pulled on the system by means of vacuum pump 116, which aids in solvent evaporation.

EXAMPLE 1

A solution of compound and polymer was made by dissolving 133.0 mg of [R-(R*S*)]-5-chloro-N-[2-hydroxy-3-(methoxymethylamino)-3-oxo-1-(phenylmethyl)propyl]-1-H-indole-2-carboxamide (Compound 1, shown below) and 67.0 mg of HPMCAS-MF (Shin Etsu, containing 23.4% methoxyl, 7.2% hydroxypropyl. 9.4% acetyl, 11.0% succinoyl, MW=80*10$^4$, Mn=4.4*10$^4$) in 10 gm of HPLC grade acetone (Burdick & Jackson). The compound/polymer solution was then placed in a 20 mL syringe that was then inserted into a syringe pump.

Compound 1

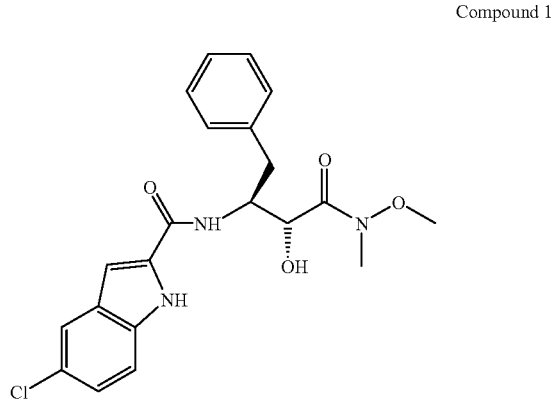

Solvent was rapidly removed from the above solution by spraying it into the mini spray-drying apparatus shown in FIG. 1, referred to herein as the "mini" spray dryer. The resulting material was a dry, white, substantially amorphous powder.

EXAMPLE 2

This example discloses an in vitro dissolution test termed the "syringe/filter" method. In this method the concentration of test compound in solution is determined as a function of time. Test solution is held in a syringe from which samples are expelled through a filter at pre-determined time points. In between expelling samples from the syringe, the syringe is rotated (50 rpm) on a wheel held in an oven at 37° C.

7.5 mg of the material of Example 1 was placed in an empty disposable 10 mL syringe (Aldrich, Fortuna). A 20 GA hypodermic needle was attached to the syringe, and 10 mL of a model-fasted duodenal (MFD) solution at 37° C. was drawn into the syringe. The MFD solution was composed of phosphate-buffered saline solution (82 mM NaCl, 20 mM $Na_2HPO_4$, 47 mM $KH_2PO_4$, pH 6.5, 290 mOsm/kg) containing 14.7 mM sodium taurocholate (Fluka) and 2.8 mM 1-palmitoyl-2-oleoyl-sn-glycero-3-phosphocholine (Avanti Polar Lipids).

The MFD solution was prepared using the following procedure. Into a 100 mL round bottom flask was weighed 0.788 gm of the sodium taurocholic acid, which was then dissolved in 5.0 mL of ambient HPLC methanol (Burdick & Jackson). To this solution was added 15.624 gm of the 1-palmitoyl-2-oleoyl-sn-glycero-3-phosphocholine in chloroform, supplied by Avanti Polar Lipids as a 20 mg/mL solution. This mixture was then mixed thoroughly by vortex mixer (Fisher Vortex Genie), and the solvent removed rapidly by roto-evaporator (Rotavapor RE121, Büchi), leaving a dry white surface dispersion coating the flask. The surface dispersion was then reconstituted with 200 mL of the 37° C. phosphate buffered saline.

The needle was then replaced with a 13 mm, 0.45 μm polyvinylidine diflouride syringe filter (Scientific Resources, Titan), and the syringe was vigorously shaken for 30 sec. After 30 sec, 6 drops of the solution was expelled and a subsequent 13 drop sample was delivered to a test tube. After expelling the sample, the syringe plunger was drawn back to pull an air bubble into the syringe to aid in subsequent mixing and the syringe placed back on a rotating wheel in a 37° C. oven. The sample was diluted 1:1 with a solution containing 60/40-1.7 wt % ammonium ascorbate in acetonitrile, and the concentration of compound analyzed on an HPLC (Hewlett Packard 1090 HPLC, Phenomenex Ultracarb ODS 20 analytical column, absorbance measured at 215 nm with a diode array spectrophotometer). The remaining solution in the syringe was mixed by rotating on a wheel at 50 rpm in a 37° C. temperature-controlled box.

Samples were taken after 5, 30, 60 and 180 minutes as described above, analyzed, and compound concentrations calculated. The concentration of compound in the filtrate as a function of elapsed time (time=0 when the solid material of Example 1 is first mixed with aqueous solution) was found to be 17 μgA/ml at 5 min., 70 μgA/ml at 10 min., 120 μgA/ml at 30 min., 127 μgA/ml at 60 min and 135 μgA/ml at 180 min., and 38 μgA/ml at 1200 min. (see Table I, Example 9). This result showed that the HPMCAS/Compound 1 solid amorphous dispersion rapidly yields a high concentration of dissolved compound (at least 12-fold higher than its equilibrium solubility of 9 μgA/ml) in the dissolution medium and this supersaturated concentration was maintained for at least 180 minutes. When crystalline compound was triturated and subjected to the same dissolution test, a maximum concentration of Compound 1 of 10 μgA/ml was obtained (See Comparative Example 1). Throughout the examples, triturated material indicates that the material was ground lightly by hand for 60 seconds using a mortar and pestle.

EXAMPLE 3

This example discloses an in vitro dissolution test termed the "centrifuge" method. This method was used to test the dissolution of material made by essentially the same method as that described in Example 1 except that the concentration of Compound 1 was decreased by a factor of 2 to 66.5 mg such that the ratio of compound to polymer was 1:1. (see Example 7, Table I).

In a 37° C. controlled temperature box, 1.8 mg of solid product from Example 1 was accurately weighed into an empty microcentrifuge tube (polypropylene, Sorenson Bioscience Inc.). The theoretical maximum concentration of compound in solution (e.g., if all compound dissolved) was 383 μgA/ml [1.8 mg dispersion (1000 μg/1 mg) (0.5 μg compound/μg dispersion) (0.764 compound assay)/1.8 ml=393 μgA/ml]. This value is termed the theoretical maximum supersaturated concentration and is abbreviated Theoretical MSSC. 1.8 mL of a 37 C phosphate buffered saline solution (8.2 mM NaCl, 1.1 mM Na2HPO4, 4.7 mM KH2PO4, pH 6.5, 290 mOsm/kg) containing 14.7 mM sodium taurocholic acid (Fluka) and 2.8 mM 1-palmitoyl-2-oleoyl-sn-glycero-3-phosphocholine (Avanti Polar Lipids) was added to the tube. The centrifuge tube was closed and a timer was started. The tube was then mixed continuously at the highest speed on a vortex mixer (Fisher Vortex Genie 2) for 60 seconds. The tube was transferred to a centrifuge (Marathon, Model Micro A) allowed to stand undisturbed for six minutes, then centrifuged at 13,000 G for 60 seconds. A 25 uL sample was removed from the solids-free supernatant in the centrifuge tube via pipette (Gilson Pipetman P-100) ten minutes after the timer was started. Solids in the centrifuge tube were resuspended by mixing the sample continuously on the vortex mixer for 30 seconds. The centrifuge tube was returned to the centrifuge and allowed to stand undisturbed until the next sample was taken. Each sample was centrifuged, sampled and resuspended as described previously. Each sample was diluted 1:1 with a solution containing 60/40 1.7wt % ammonium ascorbate/acetonitrile, and the concentration of compound was determined by HPLC (Hewlett Packard 1090 HPLC, Phenomenex Ultracarb ODS 20 analytical column, absorbance measured at 215 nm with a diode array spectrophotometer). Samples were taken after 10, 30, 60, 180, and 1,200 minutes as described above, analyzed and compound concentrations were calculated. The concentration of compound in the supernatant solution for the times listed above were 96, 121, 118, 125, and 40 μgA/ml, respectively. The composition and performance data is summarized in Table I as Example 7. The maximum compound concentration observed, 125 μgA/ml, is termed the maximum supersaturated concentration of compound and is abbreviated MSSC.

in Example 2 or Example 3 as noted in Table I and the results are tabulated in Table I.

COMPARATIVE EXAMPLES C1 TO C4

The following tests of Compound 1 were conducted to aid in demonstrating the superior solubilities of dispersions according to the invention relative to conventional forms of Compound 1. Dissolution tests were conducted using the syringe/filter test described in Example 2 with four materials: 1) triturated crystalline compound alone (Example C1), 2) a solid spray-dried dispersion of Compound 1 and PVAP (Example C2), 3) a solid spray-dried dispersion of Compound 1 and HPMCP (Example C3), and 4) a solid spray-dried dispersion of Compound 1 and PVP (Example C4). The composition of each material and the results of the dissolution tests

TABLE I

| EXAMPLE NO. | Drug No. | Polymer Type | Dg:Poly Ratio | Sprayer | Analytical Method | Theor. MSSC (μgA/mL) | MSSC (μgA/mL) | $C_{90}$ (μgA/mL) | $C_{1200}$ (μgA/mL) | $C_{180}$ (μgA/mL) |
|---|---|---|---|---|---|---|---|---|---|---|
| 5 | 1 | HPMCAS-MF | 1:1 | MINI | syringe/filter | 500 | 120 | 117 | 14 | 120 |
| 6 | 1 | HPMCAS-MF | 1:1 | MINI | syringe/filter | 500 | 82 | 80 | 20 | 82 |
| 7 | 1 | HPMCAS-MF | 1:1 | MICRO | centrifuge | 383 | 125 | 118 | 40 | 125 |
| 8 | 1 | HPMCAS-MF | 1:1 | MICRO | syringe/filter | 500 | 120 | 116 | 100 | 120 |
| 9 | 1 | HPMCAS-MF | 1:0.5 | MINI | syringe/filter | 500 | 135 | 130 | 38 | 135 |
| 10 | 1 | HPMCAS-MF | 1:1 | MICRO | syringe/filter | 500 | 117 | 115 | 36 | 115 |
| 11 | 1 | HPMCAS-MF | 1:2 | MICRO | syringe/filter | 500 | 112 | 110 | 39 | 100 |
| 12 | 1 | HPMCAS-MF | 1:5 | MICRO | syringe/filter | 500 | 108 | 96 | 96 | 95 |
| 13 | 1 | HPMCAS-MF | 1:9 | MICRO | syringe/filter | 89 | 86 | 82 | 85 | 83 |
| 14 | 1 | HPMCAS-MF | 1:9 | MINI | syringe/filter | 545 | 520 | 333 | 520 | 399 |

EXAMPLE 4

A solution of compound and polymer was made by dissolving 200.0 mg of [R-(R*,S*)]-5-chloro-N-[2-hydroxy-3-(methoxymethylamino)-3-oxo-1-(phenylmethyl)propyl]-1-H-indole-2-carboxamide (Compound 1) and 1.8 gm of HPMCAS-MF (Shin Etsu, containing 23.4% methoxyl, 7.2% hydroxypropyl, 9.4% acetyl, 11.0% succinoyl, MW=$8.0*10^{-4}$, Mn=$4.4*10^{-4}$) in 118 gm of HPLC grade acetone (Burdich & Jackson). The compound/polymer solution was then spray-dried.

Solvent was rapidly removed from the above solution by spraying it into the spray-drying apparatus shown in FIG. 2, the "micro" spray dryer. The resulting material was a dry, white, substantially amorphous powder.

EXAMPLES 5 TO 14

Spray-dried dispersions of Compound 1 exemplifying the invention were made as described in Example 1 (Mini Spray-dryer) or Example 4 (Micro Spray-dryer) except as noted in Table I. The dispersions were tested by the method described are listed in Table II and should be compared to Examples 5 to 14 in Table I. All HPMCAS dispersions showed much higher concentrations of dissolved compound (80 to 520 μgA/ml) than the crystalline compound alone (10 μgA/ml) and the compound concentration even after 1200 minutes was 20 to 520 μgA/ml, at least twice the equilibrium solubility (i.e. 8 to 10 μgA/ml). In addition it can be seen that although dispersions composed of matrix polymers other than HPMCAS (PVAP, HPMCP, PVP) show supersaturation, this super saturation is not maintained as well as with HPMCAS ($C_{1200}$ values are approximately equal to equilibrium solubility (9 to 13 μgA/ml) while $C_{1200}$ values for HPMCAS dispersions are generally 40 to 520 μgA/ml.

TABLE II

| Comparative Examples for Compound No. 1 | | | | | | | | | | |
|---|---|---|---|---|---|---|---|---|---|---|
| Example No. | Cpd No. | Polymer Type | Cpd Polymer Ratio | Sprayer | Dissolution Test Method | Theor. MSSC (μgA/mL) | MSSC (μgA/mL) | C90 (μgA/mL) | C1200 (μgA/mL) | C180 (μgA/mL) |
| C1 | 1 | NONE | 1:0 | TRITURATED | syringe/filter | 98 | 10 | 10 | 9 | 8.5 |
| C2 | 1 | PVAP | 1:1 | MINI | syringe/filter | 500 | 104 | 82 | 9 | 17 |
| C3 | 1 | HPMCP | 1:1 | MINI | syringe/filter | 500 | 127 | 123 | 13 | 106 |
| C4 | 1 | PVP | 1:1 | MINI | syringe/filter | 500 | 133 | 125 | 13 | 114 |

EXAMPLE 15

In this example, a solid amorphous dispersion of Compound 1 was prepared using a relatively large spray dryer that produces dispersions at a rate of about 0.5 to 1.0 g/min. A compound/polymer solution was made by dissolving 6 g of Compound 1 and 3 g HPMCAS-MF in 600 g of acetone. The compound/polymer solution was then placed in a pressure vessel that delivers the compound/polymer solution at a controlled rate to a commercial spray dryer. (Mobile Minor Hi- Tec for Non-Aqueous Feed Spray Dryer, manufactured by NIRO A/S, Soburg, Denmark)

The Niro spray dryer consists of an atomizer that fits into the top of a drying chamber. The atomizer is a 2-fluid nozzle. The atomizing gas was nitrogen delivered to the nozzle at and a flow of 180 g/min. The Compound/polymer solution described above was delivered to the nozzle at room temperature at a rate of 45 g/min. Drying gas was delivered to the drying chamber through an inlet duct that surrounds the 2-fluid nozzle. The drying gas was nitrogen heated to 120° C. and delivered to the drying chamber at 1500 s/min. The spray-dried material exited the chamber with the drying gas through transport ducts and into a cyclone. At the top of the cyclone is an exhaust vent that allows the nitrogen and evaporated solvent to escape. The spray-dried material was collected in a canister. The material was a dry, white, substantially amorphous powder.

This dispersion was tested by using the method described in Example 2. Sufficient dispersion was used in this test such that the theoretical maximum concentration of Compound 1 (if it all dissolved) was 500 μgA/ml. The maximum concentration of Compound 1 observed was 137 μgA/ml. Ninety minutes after the start of this test, the concentration of Compound 1 was 130 μgA/ml and at 1200 minutes the concentration was 22 μgA/ml. Comparison of these results to those for Example 9 in Table I show that the dispersion made on the large spray dryer performed similarly to that made on the "mini" spray dryer.

EXAMPLES 16 TO 18

Spray-dried dispersions of Compound 2, 3,5-dimethyl-4-(3'-pentoxy)-2-(2',4',6'-trimethylphenoxy)pyridine, structure shown below, exemplifying the invention were made as described in Example 1 (Mini Spray-dryer), except as noted in Table III. The dispersions were tested by the method described in Example 3 and noted in Table III and the results are tabulated in Table III.

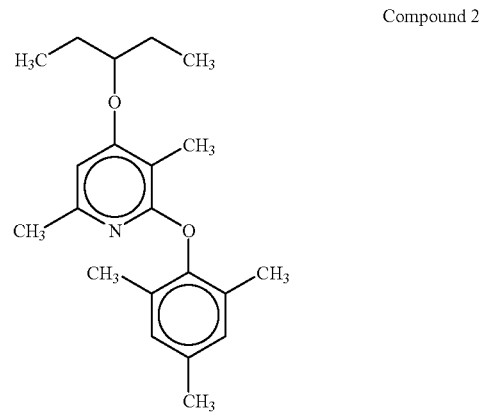

Compound 2

TABLE III

| EXAMPLE NO. | Drug No. | Polymer Type | Dg:Poly Ratio | Sprayer | Analytical Method | Theor. MSSC (μgA/mL) | MSSC (μgA/mL) | $C_{90}$ (μgA/mL) | $C_{1200}$ (μgA/mL) | $C_{180}$ (μgA/mL) |
|---|---|---|---|---|---|---|---|---|---|---|
| 16 | 2 | HPMCAS-HF | 1:9 | MN | centrifuge | 95 | 73 | 69 | 46 | — |
| 17 | 2 | HPMCAS-MF | 1:9 | MN | centrifuge | 105 | 103 | 92 | 63 | — |
| 18 | 2 | HMPCAS-MF | 1:2 | MN | centrifuge | 100 | 66 | 54 | 51 | — |

COMPARATIVE EXAMPLES C5 AND C6

The following tests of Compound 2 in crystalline form either alone or simply triturated by hand (as described in Example 2) with HPMCAS are for comparison to Examples 16 to 18 in Table III. The composition of the materials and the results of dissolution tests are shown in Table IV. Much higher compound concentrations were achieved with the HPMCAS dispersions relative to crystalline compound either alone or mixed (but not dispersed) in HPMCAS. This demonstrates that the compound should be dispersed in amorphous form in the HPMCAS according to this invention instead of triturating the crystalline compound with HPMCAS to achieve high levels of supersaturation that are maintained for long time periods.

TABLE IV

Comparative Examples for Compound No. 2

| Ex No. | Cpd No. | Polymer Type | Cpd Polymer Ratio | Sprayer | Dissolution Test Method | Theor. MSSC (μgA/mL) | MSSC (μgA/mL) | C90 (μgA/mL) | C1200 (μgA/mL) | C180 (μgA/mL) |
|---|---|---|---|---|---|---|---|---|---|---|
| C5 | 2 | None | 1:0 | TRITURATED | centrifuge | 100 | 18 | 18 | 13 | — |
| C6 | 2 | HPMCAS-HF | 1:9 | TRITURATED | centrifuge | 85 | 12 | 12 | — | — |

EXAMPLES 19 TO 22

Spray-dried dispersions of Compound 3,5-(2-(4-(3-benzisothiazolyl)-piperazinyl)ethyl-6-chlorooxindole (ziprasidone), shown below, exemplifying the invention were made as described in Example 1 (Mini Spray-dryer) except as noted in Table V. The dispersions were tested by the method described in Example 3 as noted in Table V and the results are tabulated in Table V.

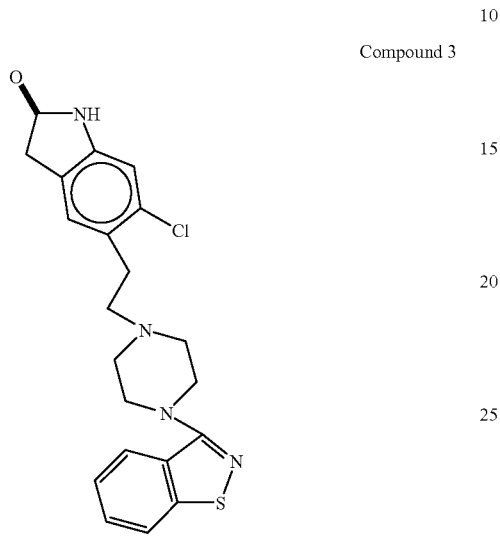

Compound 3

TABLE V

| EXAMPLE NO. | Drug No. | Polymer Type | Dg:Poly* Ratio | Sprayer | Analytical Method | Theor. MSSC (µgA/mL) | MSSC (µgA/mL) | $C_{90}$ (µgA/mL) | $C_{1200}$ (µgA/mL) | $C_{180}$ (µgA/mL) |
|---|---|---|---|---|---|---|---|---|---|---|
| 19 | 3 | HPMCAS-HF | 1:9 | MN | centrifuge | 189 | 98 | 59 | — | — |
| 20 | 3 | HMPCAS-HF | 1:5 | MN | centrifuge | 162 | 101 | 40 | 11 | — |
| 21 | 3 | HPMCAS-MF | 1:9 | MN | centrifuge | 176 | 138 | 7 | 4 | — |
| 22 | 3 | HPMCAS-LF | 1:9 | MN | centrifuge | 151 | 105 | 12 | — | — |

*Drug:Polymer ratio is based on total weight of hydrochloride salt.

COMPARATIVE EXAMPLES C7 AND C8

The following tests of Compound 3 in crystalline form alone and triturated with HPMCAS are for comparison to Examples 19 to 22 in Table V. The composition of the materials and the results of dissolution tests are shown in Table VI. The HPMCAS dispersions yielded much higher compound concentrations than either the crystalline compound alone or the crystalline compound triturated by hand with HPMCAS showing the excellent performance of the composition of the invention and the importance of dispersing the compound in HPMCAS in an amorphous form. The results shown in Table V also demonstrate that for dispersions of Compound 3, HPMCAS-HF maintains a higher compound concentration (compare $C_{90}$ values), compared to HPMCAS-MF and HPMCAS-LF.

TABLE VI

Comparative Examples for Compound No. 3

| Ex No. | Cpd No. | Polymer Type | Cpd Polymer Ratio | Sprayer | Dissolution Test Method | Theor. MSSC (µgA/mL) | MSSC (µgA/mL) | C90 (µgA/mL) | C1200 (µgA/mL) | C180 (µgA/mL) |
|---|---|---|---|---|---|---|---|---|---|---|
| C7 | 3 | NONE | 1:0 | TRITURATED | centrifuge | 180 | 27 | 4 | 1 | — |
| C8 | 3 | HPMCAS-HF | 1:5 | TRITURATED | centrifuge | 176 | 37 | 29 | 4 | — |

EXAMPLE 23

A dispersion of Compound 3 was made by dissolving 10 g of Compound 3 and 90 g of HPMCAS-HF in 2400 g methanol. This compound/polymer solution was spray-dried using the Niro spray dryer as described in Example 15. The compound/polymer solution was delivered to the 2-fluid nozzle at room temperature at a flow rate of 25 g/min. All other conditions were the same as those described in Example 15.

This dispersion was tested using the method described in Example 3 (the "centrifuge" method). Sufficient dispersion was tested such that the concentration of Compound 3 would be 200 μgA/ml if all of the compound dissolved. The maximum compound concentration observed ($C_{max}$) was 107 μgA/ml. The compound concentration after 90 minutes and 1200 minutes was 60 μgA/ml and 32 μgA/ml, respectively.

EXAMPLE 24

A comparison of the performance of dispersions of the present invention (spray dried) with those prepared conventionally by slow evaporation of solvent was made as follows. A dispersion of the present invention (Example 24) was prepared from 500 grams of compound/polymer solution comprising 0.2 wt % Compound 3 and 1.8 wt % HPMCAS-HF in methanol (USP/NF grade) using the Niro spray dryer and procedure described in Example 23. 5.8 grams of spray-dried dispersion was recovered.

COMPARATIVE EXAMPLES C9 AND C10

A conventional dispersion (Example C9) was prepared as follows. 100 grams of compound/polymer solution of the same composition as that used in Example 24 was placed in a 500 ml round-bottom flask. Solvent was removed from the solution at reduced pressure at 40° C. using a rotary evaporator. After 30 minutes, the material appeared to be dry and it was scraped from the flask. The conventional dispersion was placed under vacuum for several hours to remove any traces of solvent. 1.8 grams of conventional dispersion was recovered.

The two dispersions described above (Example 24 and Example C9) and crystalline compound (Comparative Example C10) were tested using the centrifuge method described in Example 3. The results of this test are listed in Table VII. The dispersion prepared by spray drying performed much better than dispersion prepared by conventional rotary evaporation.

TABLE VII

| Ex No. | Cpd No. | Polymer Type | Cpd Polymer Ratio | Drying Equipment | Dissolution Test Method | Theor. MSSC (μgA/mL) | C3 (μgA/mL) | C10 (μgA/mL) | C20 (μgA/mL) | C40 (μgA/mL) |
|---|---|---|---|---|---|---|---|---|---|---|
| 24 | 3 | HPMCAS-HF | 1:9 | Niro Spray Dryer | centrifuge | 195 | 128 | 98 | 75 | 47 |
| C9 | 3 | HPMCAS-HF | 1:9 | rotary evaporator | centrifuge | 204 | 0 | 0 | 0 | 3.9 |
| C10 | 3 | NONE | 1:0 | — | centrifuge | 180 | 27 | 22 | 19 | 7 |

EXAMPLES 25 TO 27

Spray-dried dispersions of Compound 4, Griseofulvin, 7-chloro-4,6-dimethoxy-courmaran-3-one-2-spiro-1'-(2'-methoxy-6'-methylcyclohex-2'en-4'-one), shown below, exemplifying the invention were made as described in Example 4 (Micro Spray-dryer) except as noted in Table VII. The dispersions were tested by the method described in Example 2 as noted in Table VII and the results are tabulated in Table VIII.

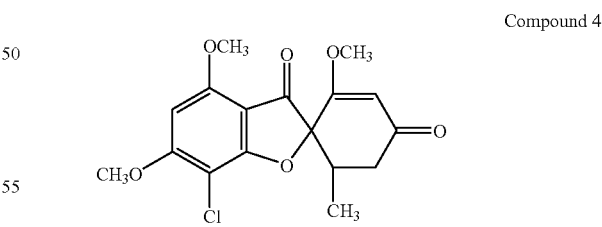

Compound 4

TABLE VIII

| EXAMPLE NO. | Drug No. | Polymer Type | Dg:Poly Ratio | Sprayer | Analytical Method | Theor. MSSC (μgA/mL) | MSSC (μgA/mL) | $C_{90}$ (μgA/mL) | $C_{1200}$ (μgA/mL) | $C_{180}$ (μgA/mL) |
|---|---|---|---|---|---|---|---|---|---|---|
| 25 | 4 | HPMCAS-MF | 1:9 | MICRO | syringe/filter | 200 | 185 | 175 | 125 | 175 |
| 26 | 4 | HPMCAS-MF | 1:4 | MICRO | syringe/filter | 200 | 175 | 165 | — | 160 |

COMPARATIVE EXAMPLE C11

This example shows the results of a dissolution test of Compound 4 in its crystalline form in Table IX for comparison with Examples 25 to 27, Table VII. Much higher compound concentrations are achieved with the HPMCAS dispersions than with crystalline compound alone.

TABLE IX

Comparative Examples for Compound No. 4

| Example No. | Cpd No. | Polymer Type | Cpd Polymer Ratio | Sprayer | Dissolution Test Method | Theor. MSSC (µgA/mL) | MSSC (µgA/mL) | C60 (µgA/mL) | C90 (µgA/mL) | C180 (µgA/mL) |
|---|---|---|---|---|---|---|---|---|---|---|
| C11 | 4 | NONE | 1:0 | TRITURATED | syringe/filter | 200 | 18 | 17 | 15 | — |

EXAMPLE 28

A spray-dried dispersion of Compound 5, nifedipine, 1,4-dihydro-2,6-dimethyl-4-(2-nitrophenyl)-3,5-pyridinecarboxylic acid dimethyl ester, structure shown below, exemplifying the invention was made as described in Example 4 (Micro Spray-dryer) except as noted in Table X. The dispersion was tested by the method described in Example 2 as noted in Table X and the results are tabulated in Table X.

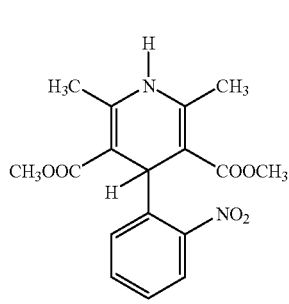

Compound 5

EXAMPLE 29 AND COMPARATIVE EXAMPLES C13 AND C14

A comparison of the performance of a dispersion of Compound 6, 5,5-diphenylhydantoin (phenytoin), shown below, and HPMCAS of the present invention (spray-dried) with those prepared conventionally by slow evaporation of solvent was made as follows. A dispersion of the present invention (Example 29) was prepared from 720 grams of a compound/polymer solution prepared by dissolving 0.10 wt % of Compound 6 (Aldrich) and 0.90 wt % HPMCAS-MF (Shin-Etsu) in acetone (HPLC grade). This compound/polymer solution was spray-dried using the Niro spray-dryer and procedure described in Example 23. 6.8 grams of spray-dried dispersion was recovered.

A conventional dispersion (Example C13) was prepared from 90 grams of a compound/polymer solution of the same composition as that used in Example 29 using the procedure described for Comparative Example C9 except that the solvent was evaporated at 30° C. After 30 minutes, the material coated the surface of the flask as a solid cake and it was scraped from the flask. 0.9 grams of product was recovered.

The two dispersions described above (Example 29 and Comparative Example C13) and crystalline compound

TABLE X

| EXAMPLE NO. | Drug No. | Polymer Type | Dg:Poly Ratio | Sprayer | Analytical Method | Theor. MSSC (µgA/mL) | MSSC (µgA/mL) | $C_{90}$ (µgA/mL) | $C_{1200}$ (µgA/mL) | $C_{180}$ (µgA/mL) |
|---|---|---|---|---|---|---|---|---|---|---|
| 28 | 5 | HPMCAS-MF | 1:9 | MICRO | syringe/filter | 100 | 105 | 90 | 88 | 95 |

COMPARATIVE EXAMPLE C12

This example shows the results of a dissolution test of Compound 5 in its crystalline form in Table XI for comparison with Example 28. A much higher compound concentration is achieved and sustained for 1200 minutes with the HPMCAS dispersion relative to crystalline compound alone.

(Comparative Example C14) were tested using the centrifuge method described in Example 3. The results of this test are listed in Table XII.

The results clearly show that over the first 40 minutes of dissolution that the dispersions of the present invention achieve significantly higher compound concentrations than

TABLE XI

Comparative Examples for Compound No. 5

| Example No. | Cpd No. | Polymer | Cpd: Polyme Ratio | Sprayer | Dissolution Test Method | Theor. MSSC (µgA/mL) | MSSC (µgA/mL) | C90 (µgA/mL) | C1200 (µgA/mL) | C180 (µgA/mL) |
|---|---|---|---|---|---|---|---|---|---|---|
| C12 | 5 | NONE | 1:0 | TRITURATED | syringe/filter | 100 | 19 | 18 | 19 | 19 | either crystalline compound (Comparative Example C14) or the conventional dispersion (Comparative Example C13).

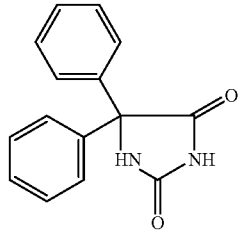

Compound 6

TABLE XII

Comparative Examples for Compound No. 6

| Example No. | Cpd No. | Polymer | Cpd:Polymer Ratio | Sprayer | Dissolution Test Method | Theor. MSSC (µgA/mL) | C3 (µgA/mL) | C10 (µgA/mL) | C20 (µgA/mL) | C40 (µgA/mL) | C90 (µgA/mL) |
|---|---|---|---|---|---|---|---|---|---|---|---|
| 29 | 6 | HPMCAS-MF | 1:9 | Niro | centrifuge | 96 | 97 | 96 | 90 | 97 | 99 |
| C13 | 6 | HPMCAS-MF | 1:9 | rotary evaporator | centrifuge | 103 | 23 | 43 | 58 | 78 | 90 |
| C14 | 6 | NONE | 1:0 | | centrifuge | 100 | 14 | 20 | 28 | 34 | 50 |

EXAMPLE 30 AND COMPARATIVE EXAMPLE C15

A spray-dried dispersion of Compound 7, (+)-N-{3-[3-(4-fluorophenoxy)phenyl]-2-cyclopenten-1-yl}-N-hydroxyurea, structure shown below, exemplifying the invention was made as described in Example 1 (Mini Spray-dryer) except as noted in Table XIII. The dispersion, along with crystalline Compound 7 (Comparative Example C15), were tested by the method described in Example 3 as noted in Table XIII and the results are tabulated in Table XIII. The observed concentration of Compound 7 was much higher for the dispersion relative to the crystalline compound.

EXAMPLE 31 AND COMPARATIVE EXAMPLE C16

A spray-dried dispersion of Compound 8, [3,6-dimethyl-2-(2,4,6-trimethyl-phenoxy)-pyridin-4-yl]-(1-ethyl-propyl)-amine, shown below, exemplifying the invention was made as described in Example 1 (Mini Spray-dryer) except as noted in Table XIV. The dispersion, along with crystalline Compound 8 (Comparative Example C16), were tested by the method described in Example 3 and noted in Table XIV and the results are tabulated in Table XIV. The observed concentration of Compound 8 was much higher for the dispersion relative to the crystalline compound.

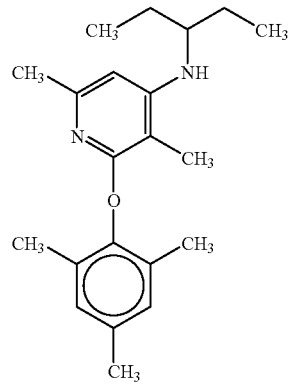

Compound 8

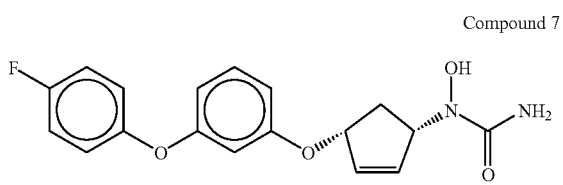

Compound 7

TABLE XIII

| EXAMPLE NO. | Drug No. | Polymer Type | Dg:Poly Ratio | Sprayer | Analytical Method | Theor. MSSC (µgA/mL) | MSSC (µgA/mL) | $C_{90}$ (µgA/mL) | $C_{1200}$ (µgA/mL) | $C_{180}$ (µgA/mL) |
|---|---|---|---|---|---|---|---|---|---|---|
| 30 | 7 | HPMCAS-HF | 1:9 | MINI | centrifuge | 1045 | 550 | 320 | 220 | — |

TABLE XIV

| EXAMPLE NO. | Drug No. | Polymer Type | Dg:Poly Ratio | Sprayer | Analytical Method | Theor. MSSC (µgA/mL) | MSSC (µgA/mL) | $C_{90}$ (µgA/mL) | $C_{1200}$ (µgA/mL) | $C_{180}$ (µgA/mL) |
|---|---|---|---|---|---|---|---|---|---|---|
| 31 | 8 | HPMCAS-LF | 1:2 | MINI | centrifuge | 477 | 467 | 405 | 167 | — |
| C16 | 8 | None | 1:0 | — | centrifuge | 500 | 22 | 22 | 22 | — |

EXAMPLE 32 AND COMPARATIVE EXAMPLE C17

A spray-dried dispersion of Compound 9, 1H-Indole-2-caboxamide, 5-chloro-N-[3-(3,4-dihydroxy-1-pyrrolidinyl)-2-hydroxy-3-oxo-1-(phenylmethnyl)propyl]-, [R-[R*,S*-(cis)]]-, exemplifying the invention was made as described in Example 1 (Mini Spray-dryer) except as noted in Table XV. The dispersion, along with crystalline Compound 9 (Comparative Example C17), were tested by the method described in Example 3 as noted in Table XV and the results are tabulated in Table XV. The observed concentration of Compound 9 was much higher for the dispersion relative to the crystalline compound.

Compound 9

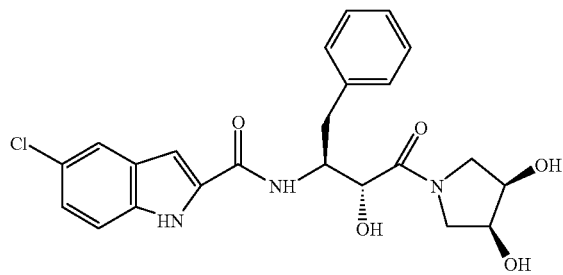

TABLE XV

| EXAMPLE NO. | Drug No. | Polymer Type | Dg:Poly Ratio | Sprayer | Analytical Method | Theor. MSSC (µgA/mL) | MSSC (µgA/mL) | $C_{90}$ (µgA/mL) | $C_{1200}$ (µgA/mL) |
|---|---|---|---|---|---|---|---|---|---|
| 32 | 9 | HPMCAS-MF | 1:1 | MN | centrifuge | 515 | 515 | 475 | 515 |
| C17 | 9 | None | 1:0 | — | centrifuge | 500 | 194 | 158 | 194 |

EXAMPLE 33

This example demonstrates that spray-dried dispersions of Compound 1 and HPMCAS, when orally dosed to beagle dogs, give a higher systemic compound exposure (Cmax and AUC) than observed after dosing an aqueous suspension of crystalline Compound 1. The following formulations were orally dosed:

Formulation A:

Aqueous suspension of crystalline Compound 1 in 0.5% methylcellulose. Dosed 5 mgA/kg at 2 ml/kg.

Formulation B

Solution of Compound 1 at 10 mgA/ml in polyethyleneglycol-400 (PEG-400). Dosed 10 mg/kg at 1 ml/kg.

Formulation C:

Aqueous suspension of a 1:1 (w/w) Compound 1/HPMCAS spray-dried dispersion at 2.5 mgA/ml in 2% polysorbate-80. Dosed at 3.7 mgA/kg at 2 ml/kg.

Formulation D:

Capsule (size#2) containing 53.1 mgA Compound 1 as a 1:1 (w/w) Compound 1/HPMCAS spray-dried dispersion. The capsule fill composition is presented in Table XVI.

Formulation E

Capsule (size #0) containing 200 mgA Compound 1 as a 2:1 (w/w) Compound 1/HPMCAS spray-dried dispersion. The capsule fill composition is presented in Table XVI.

Formulation F

Capsule (size#0) containing 200 mgA Compound 1 as a 2:1 (w/w) Compound 1/HPMCAS spray-dried dispersion. The capsule fill composition is presented in Table XVI.

Dogs were dosed either after an overnight fast, or after a meal composed of 14 g dry dog food, 8 g olive oil, and 50 ml water. Blood (3 ml) was collected from the jugular vein pre-dosing and at 0.17, 0.5, 1, 2, 4, 7, 10, 24, 32, and 48 hour post-dosing.

To 100 µl of a plasma sample, 5 ml methyl-tert-butyl ether (MTBE) and 1 ml 500 mM sodium carbonate buffer (pH 9) were added, and the sample was vortexed for 1 min, then centrifuged for 5 min. The aqueous portion of the sample was frozen in a dry ice/acetone bath and the MTBE layer was decanted and evaporated in a vortex evaporator at 55° C. The sample was reconstituted with 75 µl of a mobile phase composed of 45% acetonitrile, 55% 50 mM NaH2PO4/30 mM triethylamine (pH 3). Analysis was carried out by HPLC, using a Waters Nova-Pak C-18 column (3.9 mm×150 mm), with a C18/5 u guard column, at a temperature of 26° C., at a flow rate of 1 ml/min. Detection was by fluorescence (excitation wavelength 290 nm; emission wavelength 348 nm).

Pharmacokinetic data are presented in Table XVII. $C_{max}$ is the maximum observed plasma Compound 1 concentration, averaged over the number of dogs dosed with each formulation. AUC o-∞ is the average area under the plasma Compound 1 concentration vs. time curve.

These data demonstrate that spray-dried Compound 1/HPMCAS dispersions, when orally dosed to beagle dogs, give a higher systemic Compound 1 exposure than after dosing an aqueous suspension of crystalline Compound 1.

TABLE XVI

| Component | Formulation D | Formulation E | Formulation F |
|---|---|---|---|
| Compound 1/HPMCAS (1.1, w/w) | 44% | — | — |
| Compound 1/HPMCAS (2:1, wiw) | — | 60% | 50% |

TABLE XVI-continued

| Component | Formulation D | Formulation E | Formulation F |
|---|---|---|---|
| Lactose, fast flow | 22% | 15% | 10.8% |
| Microcrystalline Cellulose[1] | 18.8% | 15% | 32.2% |
| Sodium Starch Glycolate[2] | 8% | 7% | 5% |
| Sodium lauryl Sulfate | 2% | 2% | 1% |
| Magnesium Stearate | 1% | 1% | 1% |

[1] Avicel-102 ®
[2] Explotab ®

TABLE XVII

Canine pharmacokinetics after oral dosing of Compound 1 formulations. Canines were in fasted state, except where indicated.

| Formula-tion | Dose[1] | n[2] | Cmax (uM) | AUC 0-∞ (uMxhr/ml) | % Bioavail-ability[3] |
|---|---|---|---|---|---|
| A | 5 mgA/kg | 2 | 0.3 | 1.3 | 2.0 |
| B | 10 mgA/kg | 4 | 11.8 | 92.9 | 72.5 |
| C | 3.7 mgA/kg | 4 | 4.9 | 17.1 | 35.0 |
| D | 53.1 mgA | 3 | 3.3 | 15.8 | 31.0 |
| E | 200 mgA | 4 | 9.1 | 76.3 | 33.4 |
| F | 200 mg A | 4 | 9.0 | 82.4 | 45.6 |
| E (fed) | 200 mg A | 4 | 7.6 | 182.5 | 109.5 |

[1] For comparison purposes, the average weight of beagle dogs used in this study was around 10 kg.
[2] Number of dogs studied
[3] Relative to a 1 OmgA/kg intravenous dose given to a separate group of dogs.

EXAMPLE 34

This example demonstrates that dosing a spray dried dispersion of ziprasidone/HPMCAS to dogs results in a higher systemic ziprasidone exposure than observed after dosing crystalline ziprasidone. Systemic exposure was measured as the area under the plasma ziprasidone concentration vs. time curve (AUC).

On two occasions, after an overnight fast, five beagle dogs were dosed with 20 mgA ziprasidone in either (a) a capsule containing a spray-dried 9:1 HPMCAS-MF/Ziprasidone dispersion, or (b) a capsule containing a powder formulation of crystalline ziprasidone (30.2% ziprasidone hydrochloride, 58.6% hydrous lactose, 10% pregelatinized starch, 1.25% MgStearate). Following administration of the capsule, dogs were gavaged with 50 ml water. Water and food were witheld until 8 hr after dosing.

Pre-dosing, and at 0.5, 1, 1.5, 2, 3, 4, 6, and 8 hr post-dosing, blood samples were taken, and plasma was harvested. Ziprasidone concentration was assayed using an HPLC assay. The mobile phase consisted of 40/60 aqueous NaH2PO4 (0.005M)/acetonitrile, and the column was a CN-Chromega column, 5 u, CN+NP, 25 cm×4.6 mm (ES Industries). The flow rate was 1.5 ml/min, and detection was at 315 nm.

For the capsule containing crystalline ziprasidone, the observed average AUC(0-inf) was 561.6 ng×hr/ml. For the capsule containing the Ziprasidone/HPMCAS dispersion, the average AUC was 1056 ng×hr/ml.

The invention claimed is:

1. A spray dried solid dispersion consisting of a sparingly water-soluble drug and hydroxypropyl methylcellulose acetate succinate (HPMCAS), said drug being molecularly dispersed and amorphous in said dispersion, having a drug:polymer weight ratio between 1:0.4 and 1:20, and said dispersion is a homogeneous solid solution of said drug in said HPMCAS.

2. The spray dried solid dispersion of claim 1, wherein said drug is amorphous when undispersed.

3. The spray dried solid dispersion of claim 1, in the form of particles less than 100 μm in diameter.

4. A composition as defined in claim 1 wherein said drug is a glycogen phosphorylase inhibitor.

5. A composition as defined in claim 1 wherein said drug is

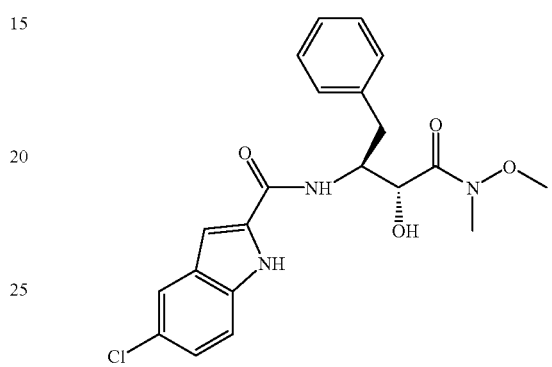

or a pharmaceutically acceptable salt thereof.

6. A composition as defined in claim 1 wherein said drug is

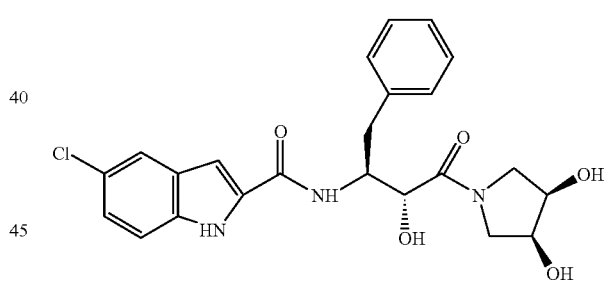

or a pharmaceutically acceptable salt thereof.

7. A composition as defined in claim 1 wherein said drug is a 5-lipoxygenase inhibitor.

8. A composition as defined in claim 1 wherein said drug is

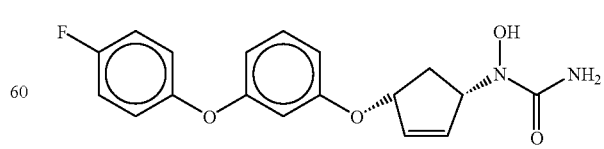

or a pharmaceutically acceptable salt thereof.

9. A composition defined in claim 1 wherein said drug is a corticotropic releasing hormone (CRH) inhibitor.

10. A composition as defined in claim 1 wherein said drug is

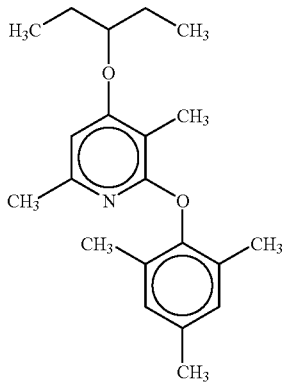

or a pharmaceutically acceptable salt thereof.

11. A composition as defined in claim 1 wherein said drug is

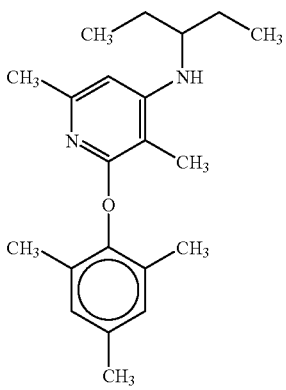

or a pharmaceutically acceptable salt thereof.

12. The spray dried solid dispersion of claim 1, wherein said drug is an antipsychotic.

13. The spray dried solid dispersion of claim 1, wherein said drug is ziprasidone.

14. A composition as defined in claim 1 wherein said drug is selected from griseofulvin, nifedipine, and phenytoin.

15. The spray dried solid dispersion of claim 1, wherein said dispersion comprises spray dried particles that are solidified in less than 2 seconds.

16. The spray dried solid dispersion of claim 1, in the form of particles having a residual solvent content less than 2 wt %.

17. The spray dried solid dispersion of claim 1, in the form of spray dried particles from a solution in which the concentration of drug in the solvent is less than 20 g/100 g and in which the total solids content is less than 25 weight %.

18. The spray dried solid dispersion of claim 1, wherein said drug has a dose to aqueous solubility ratio greater than 100.

19. The spray dried solid dispersion of claim 1, wherein said drug is crystalline when undispersed.

20. The spray dried solid dispersion of claim 1, having a drug:polymer weight ratio between 1:0.5 and 1:20.

21. The spray dried solid dispersion of claim 1, having a drug:polymer weight ratio between 1:1 and 1:20.

22. The spray dried solid dispersion of claim 1, wherein said drug is selected from the group consisting of glycogen phosphorylase inhibitors, 5-lipoxygenase inhibitors, corticotropic releasing hormone inhibitors, griseofulvin, nifedipine, and phenytoin.

23. The spray dried solid dispersion of claim 1, wherein said spray dried solid dispersion is supersaturated in said drug.

* * * * *